(12) United States Patent
Kitagawa et al.

(10) Patent No.: US 6,706,748 B2
(45) Date of Patent: Mar. 16, 2004

(54) ISOTHIAZOLE DERIVATIVES

(75) Inventors: Yoshinori Kitagawa, Tochigi (JP); Koichi Ishikawa, Tochigi (JP); Haruko Sawada, Ibaraki (JP); Yasuo Araki, Tochigi (JP); Takuma Shigyo, Tochigi (JP); Lutz Assmann, Langenfeld (DE)

(73) Assignee: Nihon Bayer Agrochem, K.K., Tokyo (JP)

( * ) Notice: Subject to any disclaimer, the term of this patent is extended or adjusted under 35 U.S.C. 154(b) by 52 days.

(21) Appl. No.: 10/257,108

(22) PCT Filed: Apr. 4, 2001

(86) PCT No.: PCT/EP01/03805

§ 371 (c)(1), (2), (4) Date: Oct. 9, 2002

(87) PCT Pub. No.: WO01/77090

PCT Pub. Date: Oct. 18, 2001

(65) Prior Publication Data

US 2003/0220197 A1 Nov. 27, 2003

(30) Foreign Application Priority Data

Apr. 12, 2000 (JP) .......................................... 2000-110530

(51) Int. Cl.$^7$ ........................ C07D 275/03; A01N 43/80
(52) U.S. Cl. ........................................ 514/372; 548/214
(58) Field of Search ............................ 514/372; 548/214

(56) References Cited

U.S. PATENT DOCUMENTS

| 4,652,303 A | 3/1987 | Watson et al. ................. 71/88 |
| 6,552,056 B2 * | 4/2003 | Assmann et al. ........... 514/372 |

OTHER PUBLICATIONS

Shin Jikken Kagaku Koza, vol. 14, Syntheses and Reactions of Organic Compounds (month unavailable) 1978, pp. 1803–1806 (Translation Attached).
Synthetic Communications, 10(3), 221–224 (month unavailable) 1980, A Non–Organometallic Method for the Synthesis of Methyl Ketones from Acyl Chlorides by T.A. Hase and K. Salonen.

\* cited by examiner

*Primary Examiner*—Robert Gerstl
(74) *Attorney, Agent, or Firm*—Richard E. L. Henderson

(57) ABSTRACT

The present invention relates to novel isothiazole derivatives of the formula

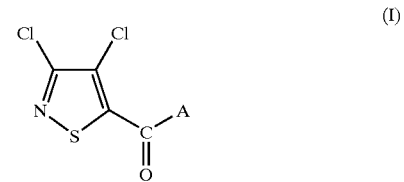

(I)

wherein A represents a group selected from

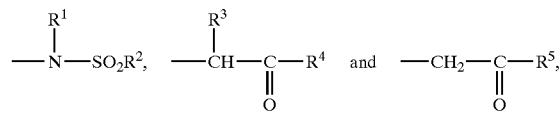

in which $R^1$, $R^2$, $R^3$, $R^4$, and $R^5$ have the meanings given in the specification, to processes for the preparation of the novel compounds, and to their use as microbicides.

7 Claims, No Drawings

ISOTHIAZOLE DERIVATIVES

The present invention relates to novel isothiazole derivatives, to processes for their preparation and to their use as microbicides.

It has already been known that certain isothiazolecarboxylic acid derivatives can be employed for the control of plants pests (see JP-A 59 024-1933 and JP-A 277 277-1996). The fungicidal activity of such known compounds, however, is not always satisfactory.

There have now been found novel isothiazole derivatives of the formula

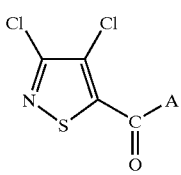

(I)

wherein

A represents a group selected from

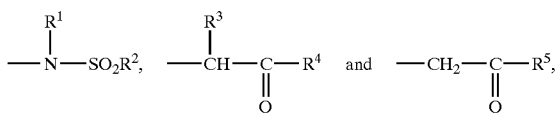

in which $R^1$ represents a hydrogen atom, $C_{1-6}$ alkyl, $C_{3-6}$ cycloalkyl, $C_{3-6}$ alkenyl, $C_{3-6}$ alkinyl, $C_{3-6}$ epoxyalkyl, 1-($C_{1-4}$ alkoxycarbonyl)$C_{1-6}$ alkyl, or $R^1$ represents phenyl optionally substituted by 1 to 3 radicals selected from halogen, $C_{1-6}$ alkyl, nitro, cyano and/or hydroxyl, or $R^1$ represents $C_{1-6}$ alkoxycarbonyl, di-($C_{1-6}$ alkyl)-amino or N—$C_{1-6}$ alkylanilino, $R^2$ represents $C_{1-18}$ alkyl or $C_{1-6}$ haloalkyl, or represents phenyl optionally substituted by 1 to 5 radicals selected from halogen, $C_{1-6}$ alkyl $C_{1-6}$ haloalkyl, $C_{1-6}$ alkoxy, $C_{1-6}$ halo-alkoxy, phenyl, cyano, amino, hydroxy, nitro and/or phenoxy, which in turn may be substituted by 1 to 3 radicals selected from halogen and/or cyano, or represents naphthyl optionally substituted by di-($C_{1-4}$ alkyl)-amino, or represents a 5-membered heterocyclic group comprising 1 or 2 hetero atoms selected from nitrogen, oxygen and/or sulfur, said heterocyclic ring being optionally substituted by up to 3 identical or different radicals selected from halogen, $C_{1-6}$ alkyl and $C_{1-4}$ alkoxycarbonyl, or represents $C_{7-9}$ aralkyl, $C_{2-4}$ alkenyl, phenyl-$C_{2-4}$ alkenyl, di-($C_{1-6}$ alkyl)-amino or camphor-10-yl, $R^3$ represents $C_{1-4}$ alkoxycarbonyl, cyano or phenylsulfonyl, $R^4$ represents phenyl optionally substituted by 1 to 3 identical or different radicals selected from $C_{1-4}$ alkyl and $C_{1-4}$ alkoxy, or represents furyl optionally substituted by 1 to 3 identical or different $C_{1-4}$ alkyl radicals, or represents $C_{1-6}$ alkoxy, or $R^3$ and $R^4$, together with the carbon atoms they are bonded to, may form a phenyl-substituted cyclohexanedione ring, wherein the phenyl ring may be substituted by halogen, and $R^5$ represents phenyl optionally substituted by 1 to 5 identical or different radicals selected from halogen, $C_{1-10}$ alkyl $C_{3-6}$ cycloalkyl, $C_{1-6}$ haloalkyl, $C_{2-4}$ alkinyl, phenyl-$C_{2-4}$ alkinyl, $C_{1-6}$ alkoxy, $C_{1-6}$ haloalkoxy, $C_{1-4}$ alkoxymethoxy, benzyloxy (which may be substituted by halogen and/or nitro), phenyl (which may be substituted by halogen), phenoxy (which may be substituted by halogen, $C_{1-4}$ alkoxy and/or nitro), $C_{1-4}$ alkoxycarbonyl, 5- or 6-membered heterocyclyl comprising 1 or 2 nitrogen atoms or comprising 1 nitrogen atom and 1 oxygen atom (which heterocyclic ring may be substituted by 1 to 3 identical or different radicals selected from halogen, $C_{1-4}$ alkyl and/or oxo), di-($C_{1-4}$ alkyl)-amino, $C_{1-4}$ alkylthio, phenylthio, phenylsulfonyl, hydroxy, nitro and cyano, or two adjacent substituents may form a $C_{1-4}$ alkylenedioxy group or a $C_{3-8}$ alkylene group, or represents naphthyl, which may be substituted by 1 to 3 identical or different radicals selected from halogen, $C_{1-4}$ alkyl and $C_{1-4}$ alkoxy, or represents a 5- or 6-membered heterocyclic group comprising 1 to 3 hetero atoms selected from nitrogen, oxygen and/or sulfur, which heterocyclic ring may be substituted by up to 3 radicals selected from halogen, $C_{1-6}$ alkyl, phenyl and/or nitro, and which heterocyclic group may also be condensed with a benzene ring.

Further, it has been found that isothiazole derivatives of the formula (I) can be prepared by several processes. Thus, a) the compounds of the formula (I), in which A represents a group of the formula

wherein $R^1$ and $R^2$ have the above-mentioned meanings, can be prepared by reacting 3,4-dichloro-isothiazole-5-carbonyl chloride of the formula

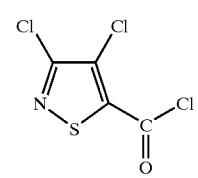

(II)

with sulfonylamino compounds of the formula

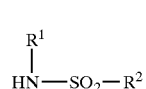

(III)

in which $R^1$ and $R^2$ have the above-mentioned meanings, in the presence of an inert diluent and, if appropriate, in the presence of an acid-binding agent.

or
b) the compounds of the formula (I), in which
   A represents a group of the formula

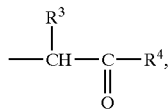

wherein
   $R^3$ and $R^4$ have the above-mentioned meanings,
   can be prepared by reacting 3,4-dichloro-isothiazole-5-carbonyl chloride of the formula

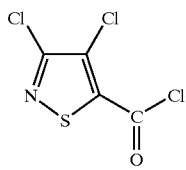

(II)

with carbonyl compounds of the formula

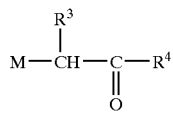

(IV)

in which
   $R^3$ and $R^4$ have the above-mentioned meanings and
   M represents lithium, sodium or potassium,
   in the presence of an inert diluent and, if appropriate, in the presence of an acid-binding agent.
or
c) the compounds of the formula (I), in which
   A represents a group of the formula

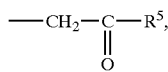

wherein
   $R^5$ has the above-mentioned meanings,
   can be prepared by reacting isothiazolecarboxylic acid derivatives of the formula

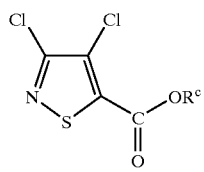

(V)

in which
   $R^c$ represents $C_{1-4}$ alkyl,
   with ketones of the formula

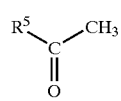

(VI)

in which
   $R^5$ has the above-mentioned meanings,
   in the presence of an inert diluent and, if appropriate, in the presence of an acid-binding agent, or
d) the compounds of the formula (I), in which
   A represents a group of the formula

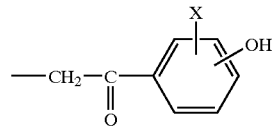

wherein
   X represents a hydrogen atom or halogen,
   can be prepared by reacting isothiazole derivatives of the formula

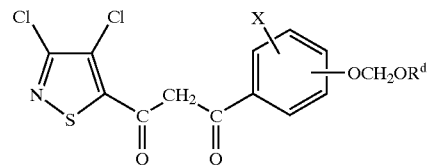

(I')

in which
   X has the above-mentioned meanings and
   $R^d$ represents $C_{1-4}$ alkyl,
   in the presence of water and an inert organic diluent and if appropriate, in the presence of an acid catalyst.

Finally, it has been found that the isothiazole derivatives of the formula (I) are outstandingly active as microbicides in agriculture and horticulture, particularly as fungicides for the direct control of plant diseases or for causing resistance in plants against plant pathogens.

Surprisingly, the isothiazole derivatives of the formula (I) according to the invention have a much better microbicidal activity than the already known compounds, which are structurally most similar and have the same type of action.

In the present context, "halogen" and "halo" in "haloalkyl" and "haloalkoxy" represents fluoro, chloro, bromo or iodo, and preferably is fluoro, chloro or bromo.

"Alkyl" represents straight-chain or branched groups, such as methyl, ethyl, n- or iso-propyl, n-, iso-, sec- or tert-butyl n- or iso-pentyl, tert-amyl, pentan-3-yl, neopentyl n-hexyl, n-heptyl n-octyl, n-nonyl n-decyl, n-pndecyl, n-dodecyl, n-tridecyl, n-tetradecyl, n-pentadecyl, n-hexadecyl, n-heptadecyl, n-octadecyl and so on.

"Alkoxy" represents straight-chain or branched groups, such as ethoxy, propoxy, isopropoxy, n-, iso-, sec- or tert-butoxy, n-pentyloxy, n-hexyloxy and so on.

The alkoxy part in "alkoxycarbonyl" and in "alkoxymethoxy" can have the same meanings as mentioned above for "alkoxy" and there may be specifically mentioned as "alkoxycarbonyl", for example, methoxycarbonyl, ethoxycarbonyl, propoxycarbonyl isopropoxycarbonyl n-, iso-, sec- or tert-butoxycarbonyl etc. and as "alkoxymethoxy", for example, methoxymethoxy, ethoxymethoxy, propoxymethoxy, isopropoxymethoxy, n-, iso-, sec- or tert-butoxymethoxy and so on.

The alkoxy part and the alkyl part in "alkoxycarbonylalkyl" can each have the same meanings as mentioned above for "alkoxy" and "alkyl" respectively and there may be specifically mentioned as "alkoxycarbonylalkyl", for example, methoxycarbonylmethyl, ethoxycarbonylmethyl, propoxycarbonylmethyl, isopropoxycarbonylmethyl, n-, iso-, sec- or tert-butoxycarbonylmethyl, 1-(methoxycarbonyl)ethyl, 2-(methoxycarbonyl)-ethyl, 1-(methoxycarbonyl)-1-methylethyl, 1-(methoxycarbonyl)-propyl, 3-(methoxycarbonyl)-propyl 1-(methoxycarbonyl)-butyl, 1-(methoxycarbonyl)-2-methylpropyl, 1-(methoxycarbonyl)-pentyl, 1-(methoxycarbonyl)-2-methylbutyl and so on.

"Alkylthio" represents straight-chain or branched groups, such as methylthio, ethylthio, propylthio, isopropylthio, n-butylthio and so on.

"Cycloalkyl" includes, for example, cyclopropyl, cyclopentyl, cyclohexyl, cycloheptyl, cyclooctyl and so on.

As "alkenyl" there may be mentioned, for example, vinyl, allyl 1-methylallyl, 1,1-dimethylallyl, 2-butenyl and so on.

As "alkinyl" there may be mentioned, for example, ethinyl, propargyl 1-methylpropargyl, 1,1-dimethylpropargyl and so on.

"Haloalkyl" can be straight chain or branched and there may be mentioned, for example, difluoromethyl, trifluoromethyl, 2-fluoroethyl, 2-chloroethyl, 2-bromoethyl, 2,2,2-trifluoroethyl, 1,1,2,2-tetrafluoroethyl, 1,1,2,2,2-pentafluoroethyl, 3-chloropropyl, 2,2,3,3,3-pentafluoropropyl, perfluorobutyl and so on.

The haloalkyl part in "haloalkoxy" can have the same meanings as mentioned above for "haloalkyl" and there may be specifically mentioned as "haloalkoxy", for example, difluoromethoxy, trifluoromethoxy, 2-fluoroethoxy, 2-chloroethoxy, 2-bromoethoxy, 2,2,2-trifluoroethoxy, 3-chloropropoxy and so on.

As "dialkylamino" there may be mentioned, for example, dimethylamino, dimethylamino, methylethylamino, methyl-n-propylamino, methyl-isopropylamino, dipropylamino, di-(n-butyl)amino, di-(n-pentyl)-amino, di-(n-hexyl)amino and so on.

As "N-alkylanilino" there may be mentioned, for example, N-methylanilino, N-ethylanilino, N-n- or iso-propylanilino, N-n-, iso-, sec or tert-butylanilino, N-n-pentylanilino, N-n-hexylanilino and so on.

"Alkylene" can be straight-chain or branched and there may be mentioned, for example, trimethylene, tetramethylene, pentathylene, 1,1-dimethyltrimethylene, 1,1,4,4-tetramethyltetramethylene and so on.

"Alkylenedioxy" includes; for example, methylenedioxy, ethylenedioxy, trimethylenedioxy and so on.

"Epoxyalkyl" is a cyclic ether formed by bonding an oxygen atom with 2 adjacent carbon atoms of an alkyl group and there may be mentioned, for example, 2,3-epoxypropyl, 2,3-epoxybutyl, 2,4-epoxybutyl and so on Heterocyclic groups in "5-membered heterocyclic groups containing 1 or 2 hetero atoms selected from the group consisting of nitrogen, oxygen, and sulfur", "5- or 6-membered heterocyclic groups containing 1 or 2 nitrogen atoms or containing 1 nitrogen atom and 1 oxygen atom" and "5- or 6-membered heterocylic groups, containing 1 to 3 hetero atoms selected from the group consisting of nitrogen, oxygen and/or sulfur atom" include saturated heterocyclic groups, unsaturated heterocylic groups and aromatic heterocyclic groups.

As "5-membered or 6-membered saturated heterocylic groups" there may be mentioned univalent groups, such as pyrrolidine, tetrahydrofuran, imidazolidine, pyrazolidine, oxazolidine, thiazolidine, piperidine, tetrahydropyran, piperazine, morpholine, 1,3-dioxolane, 1,3-dioxane etc. These heterocyclic groups may be substituted with 1 or more radicals selected from halogen (for example, fluoro, chloro, bromo etc.), oxo, alkyl (for example, methyl, ethyl, n- or iso-propyl, n-, sec-, iso-, or tert-butyl etc.), alkoxycarbonyl (for example methoxycarbonyl, ethoxycarbonyl etc.), phenyl and nitro, and in case of two or more substituents, they may be identical or different.

As "5-membered or 6-membered unsaturated heterocyclic groups" there may be mentioned univilent groups, such as 2-pyrroline, 2-pyrazoline, 3-pyrazoline, 2-imidazoline, 2-oxazoline, 2-thiazoline, 1,4-dihydropyridine, 1,2,3,4-tetrahydropyridine, 5,6-dihydro-4H-1,4-oxazine, 5,6-dihydro-4H-1,3-oxazine, 5,6-dihydro-4H-1,3-thiazine, 1,4-dihydropyridazine etc. These heterocyclic groups may be substituted with 1 or more radicals selected from halogen (for example, fluoro, chloro, bromo etc.), oxo, alkyl (for example, methyl, ethyl n- or iso-propyl, n-, sec-, iso-, or tert-butyl etc.), alkoxycarbonyl (for example methoxycarbonyl, ethoxycarbonyl etc.), phenyl and nitro, and in case of two or more substituents, they may be identical or different.

As "5- or 6-membered aromatic heterocyclic groups" there may be mentioned univalent groups, such as furan, pyrrole, thiophene, imidazole, pyrazole, oxazole, isoxazole, thiazole, isothiazole, 1,2,4-triazole, 1,3,4-thiadiazole, 1,2,3-thiadiazole, tetrazole, pyridine, pyridazine, pyrilidine, pyrazine etc. These heterocyclic groups may be substituted with 1 or more radicals selected from oxo, nitro, halogen (for example, fluoro, chloro, bromo etc.), alkyl (for example, methyl, ethyl, n- or iso-propyl, n-, sec-, iso-, or tert-butyl etc.), alkoxycarbonyl (for example methoxycarbonyl, ethoxycarbonyl etc.) and phenyl, and in case of two or more substituents, they may be identical or different.

Heterocyclic groups "which may be condensed with a benzene ring" are benzo-condensed groups of the heterocycles mentioned as examples of the above-mentioned "5- or 6-membered aromatic heterocyclic groups" and as specific examples there may be mentioned univalent groups, such as benzo[b]thiophene, benzothiazole, benzimidazole, benzotriazole, quinoline, 2,3-diydrobenzo[b]furan, benzo[d] 1,2,3-thiadiazole etc. These condensed heterocyclic groups may be substituted with 1 or more radicals selected from nitro, halogen (for example, fluoro, chloro, bromo etc.), alkyl (for example, methyl, ethyl, n- or iso-propyl, n-, sec-, iso-, or tert-butyl etc.), alkoxycarbonyl (for example methoxycarbonyl, ethoxycarbonyl etc.), oxo and phenyl, and in case of two or more substituents, they may be identical or different.

Formula (I) provides a general definition of the isothiazole derivatives according to the invention. Preferred compounds of the formula (I) are those, in which A resents a group selected from

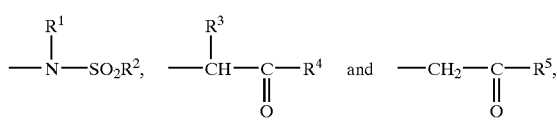

wherein $R^1$ represents a hydrogen atom, $C_{1-6}$ alkyl, $C_{5-6}$ cycloalkyl $C_{3-4}$ alkenyl, $C_{3-4}$ alkinyl, $C_{3-4}$ epoxyalkyl, 1-($C_{1-2}$ alkoxycarbonyl)-$C_{1-4}$ alkyl or represents phenyl, which may be substituted by 1 to 3 identical or different radicals selected from fluoro, chloro, bromo, $C_{1-4}$ alkyl, nitro, cyano and hydroxy, or $R^1$ represents $C_{1-4}$ alkoxycarbonyl, di-($C_{1-4}$ alkyl)-amino or N—$C_{1-4}$ alkylanilino, $R^2$ represents $C_{1-18}$ alkyl, $C_{1-4}$ haloalkyl or phenyl, which may be substituted by 1 to 5 radicals selected from fluoro, chloro, bromo, $C_{1-5}$ alkyl, $C_{1-4}$ haloalkyl, $C_{1-4}$ alkoxy, $C_{1-4}$ haloalkoxy, phenyl, cyano, amino, hydroxy, nitro and phenoxy, which in turn may be substituted by 1 to 3 identical or different substituents selected from fluoro, chloro, bromo and/or cyano, or $R^2$ represents naphthyl, which may be substituted by 1 or 2 di-($C_{1-2}$ alkyl)-amino groups, or $R^2$ represents a 5-membered heterocyclic group comprising 1 or 2 heteroatoms selected from nitrogen, oxygen and/or sulfur, said heterocylic ring being optionally substituted by up to 3 identical or different radicals selected from fluoro, chloro, $C_{1-4}$ alkyl, and $C_{1-2}$ alkoxycarbonyl, or $R^2$ represents phenyl-$C_{1-2}$ alkyl, $C_{2-3}$ alkenyl, phenyl-$C_{2-3}$ alkenyl di-($C_{1-4}$ alkyl)-amino or camphor-10-yl, $R^3$ represents $C_{1-2}$ alkoxycarbonyl, cyano or phenylsulfonyl, $R^4$ represents phenyl which may be substituted by 1 to 3 identical or different $C_{1-2}$ alkyl groups or $C_{1-4}$ alkoxy groups, or $R^4$ represents furyl, which may be substituted by 1 to 3 identical or different $C_{1-2}$ alkyl groups, or $R^4$ represents $C_{1-4}$ alkoxy, or $R^3$ and $R^4$, together with the carbon atoms they are bonded to, form a phenyl-substituted cyclohexanedione ring, wherein the phenyl ring may be mono- or di-substituted by fluoro and/or chloro, and $R^5$ represents phenyl, which may be substituted by 1 to 5 identical or different radicals selected from fluoro, chloro, bromo, iodo, $C_{1-9}$ alkyl $C_{5-6}$ cycloalkyl, $C_{1-4}$ haloalkyl, phenylethinyl, $C_{1-6}$ alkoxy, $C_{1-4}$ haloalkoxy, $C_{1-3}$ alkoxymethoxy, benzyloxy (which may be substituted by 1 to 3 identical or different radicals selected from fluoro, chloro and/or nitro), phenyl (which may be substituted by 1 to 3 radicals selected from chloro and/or bromo), phenoxy, (which may be substituted by 1 to 3 identical or different radicals selected from chloro, $C_{1-2}$ alkoxy and nitro), $C_{1-2}$ alkoxycarbonyl, 5- or 6-membered heterocyclyl comprising 1 or 2 nitrogen atoms or comprising 1 nitrogen atom and 1 oxygen atom (which heterocyclic ring may be substituted by 1 to 3 identical or different radicals selected from chloro, $C_{1-2}$ alkyl and oxo), di-($C_{1-2}$ alkyl)amino, $C_{1-2}$ alkylthio, phenylthio, phenylsulfonyl, hydroxy, nitro and cyano, or two adjacent substituents may form a $C_{1-3}$ alkylenedioxy group or a $C_{3-8}$ alkylene group, or $R^5$ represents naphthyl, which may be substituted by 1 to 3 identical or different radicals selected from fluoro, chloro, methyl, ethyl and methoxy, or $R^5$ represents a 5- or 6-membered heterocyclic group comprising 1 to 3 hetero atoms selected from nitrogen, oxygen and/or sulfur, which heterocyclic ring may be substituted by up to 3 radicals selected from fluoro, chloro, bromo, $C_{1-4}$ alkyl, phenyl and/or nitro, and which heterocyclic group may also be condensed with a benzene ring.

Particularly preferred are those compounds of the formula (I), in which

A represents a group selected from

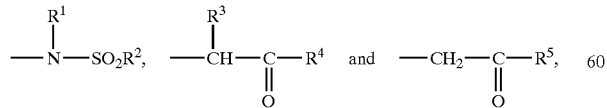

wherein $R^1$ represents a hydrogen atom, methyl, ethyl, isopropyl, n-butyl, 1,3-dimethylbutyl, cyclohexyl, allyl, propargyl, 2,3-epoxypropyl, 2-methyl-1-methoxycarbonylpropyl or represents phenyl, which may be substituted by 1 to 3 identical or different radicals selected from fluoro, chloro, bromo, methyl, nitro, cyano and hydroxy, or $R^1$ represents tert-butoxycarbonyl, dimethylamino or N-methylanilino, $R^2$ represents $C_{1-18}$ alkyl, 3-chloropropyl, trifluoromethyl, 2,2,2-tri-fluoroethyl or represents phenyl, which may be substituted by 1 to 5 identical of different radicals selected from fluoro, chloro, bromo, $C_{1-5}$ alkyl trifluoromethoxy, trifluoromethyl, methoxy, phenyl, cyano, amino, hydroxy, nitro and phenoxy, which in turn may be substituted by 1 to 3 identical or different substituents selected from fluoro, chloro, bromo and/or cyano, or $R^2$ represents naphthyl, which may be substituted by dimethylamino, or $R^2$ represents thienyl, isoxazolyl or pyrazolyl, which radicals may be substituted by up to 3 substituents selected from fluoro, chloro, methyl and/or methoxycarbonyl, or $R^2$ represents benzyl, allyl, dimethylamino or camphor-10-yl, $R^3$ represents methoxycarbonyl, ethoxycarbonyl, cyano or phenylsulfonyl $R^4$ represents phenyl, which may be substituted by 1 to 3 identical or different radicals selected from methyl, methoxy and isopropoxy, or $R^4$ represents furyl, which may be substituted by 1 to 3 identical or different radicals selected from methyl and ethyl, or $R^4$ represents methoxy or isopropoxy, or $R^3$ and $R^4$, together with the carbon atoms they are bonded to, form a phenyl-substituted cyclohexanedione ring, wherein the phenyl ring may be substituted by chloro, and $R^5$ represents phenyl which may be substituted by 1 to 5 identical or different radicals selected from fluoro, chloro, bromo, iodo, $C_{1-9}$ alkyl, cyclohexyl, trifluoromethyl, phenylethinyl, $C_{1-6}$ alkoxy, trifluoromethoxy, difluoromethoxy, ethoxymethoxy, benzyloxy (which may be substituted by 1 to 3 identical or different radicals selected from fluoro, chloro and nitro), phenyl (which may be substituted by 1 to 3 radicals selected from chloro and bromo), phenoxy (which may be substituted by 1 to 3 identical or different radicals selected from chloro, methoxy and nitro), methoxycarbonyl, ethoxycarbonyl morpholinyl, pyrrolidinyl, piperidinyl, pyridinyl or imidazolyl (each or which heterocycles may be mono- or di-substituted by methyl and/or chloro), the radical of the formula

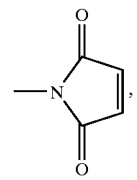

dimethylamino, methylthio, phenylthio, phenylsulfonyl, hydroxy, nitro and cyano, or two adjacent substituents may form a $C_{1-3}$ alkylenedioxy group or a $C_{3-8}$ alkylene group, or $R^5$ represents naphthyl, which may be substituted by 1 to 3 identical radicals selected from fluoro, chloro, methyl and methoxy, or $R^5$ represents a heterocyclic group selected from pyrrolyl, furanyl, dihydrofuranyl, thienyl thiazolyl, 1,2,3-thiadiazolyl pyridyl, pyrimidinyl and pyrazolyl, which radicals may be substituted by up to 3 substituents selected from fluoro, chloro, methyl phenyl and/or nitro, and which heterocyclic groups may also be condensed with a benzene ring.

If 3,4-dichloro-isothiazole-5-carbonyl chloride and N-(4-chlorophenyl)-4-methoxy-benzene-sulfonamide are used as starting materials, process (a) according to the invention can be illustrated by the following formula scheme.

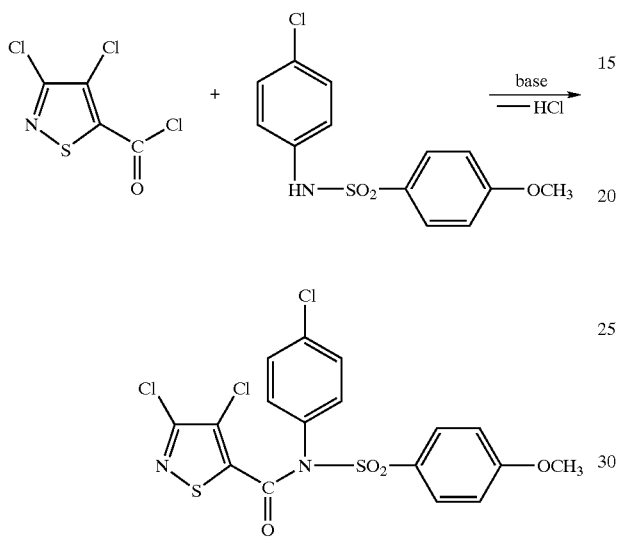

If 3,4-dichloro-isothiazole-5-carbonyl chloride and methyl cyanoacetate sodium salt are used as starting materials, process (b) according to the invention can be illustrated by the following formula scheme.

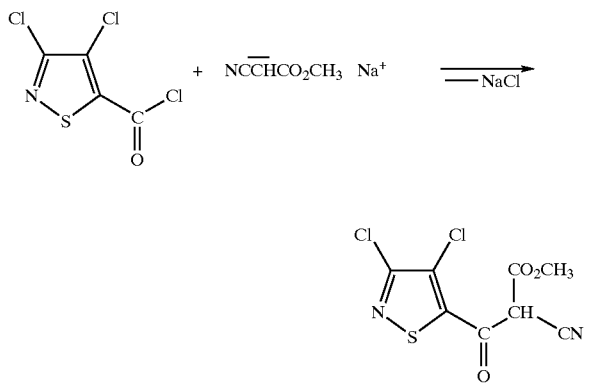

If methyl 3,4-dichloroisothiazole-5-carboxylate and 4-methoxyacetophenone are used as starting materials, process (c) according to the invention can be illustrated by the following formula scheme.

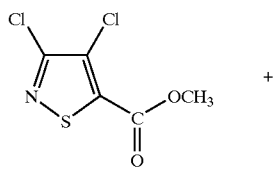

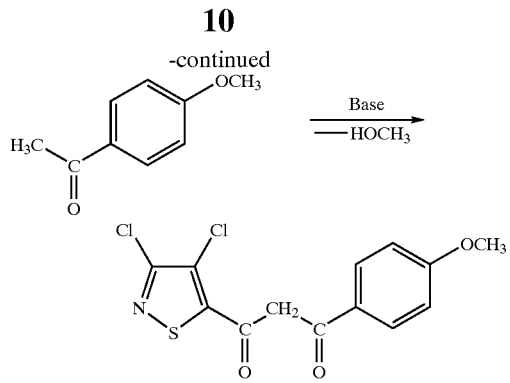

If 1-(3,4-dichloro-isothiazol-5-yl)-3-(4-ethoxymethoxy-phenyl)-1,3-propandione is used as starting material and concentrated hydrochloric acid is employed as hydrolysing agent, process (d) according to the invention can be illustrated by the following formula scheme.

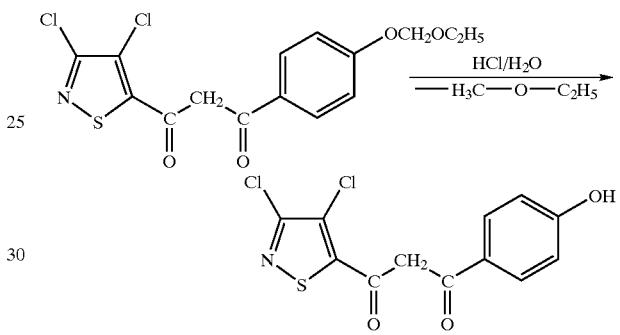

Formula (II) characterizes the 3,4-dichloro-isothiazole-5-carbonyl chloride, which is required as starting material for carrying out processes (a) and (b) according to the invention. The 3,4-dichloro-isothiazole-5-carbonyl chloride is known (see JP-A 59 024-1993).

Formula (III) provides a general definition of the sulfonylamino compounds, which are required as reaction components for carrying out process (a) according to the invention. In this formula, $R^1$ and $R^2$ preferably have those meanings, which have already been mentioned as preferred for these radicals.

The following compounds may be mentioned as examples of sulfonylamino compounds of the formula (III):
  3-Chloro-N-(4-chlorophenyl)propanesulfonamide,
  N-(4-chlorophenyl)-10-camphorsulfonamide,
  N-chloro-N-(4-nitrophenyl)-benzenesulfonamide,
  N-(2,4-dichlorophenylsulfonyl)valine methyl ester,
  N-isopropyl-2,5-dichloro-3-thienylsulfonamide,
  N-cyclohexylmethanesulfonamide,
  N-isopropyl-N',N'-dimethylsulfamide,
  5-chloro-1,3-diethylopyrazolesulfonamide,
  N',N'-dimethyl-N-methanesulfonylhydrazine and so on.

The sulfonylamino compounds of the formula (III) are known or can be prepared according to known processes [see "SHIN JIKKEN KAGAKU KOZA (New Lecture of Experimental Chemistry)" Vol. 14, "Syntheses and Reactions of Organic Compounds III", p.1803–1806 (published by Maruzen on Feb. 20, 1978)].

Formula (IV) provides a general definition of the carbonyl compounds, which are required as reaction components for carrying out process (b) according to the invention. In this formula, $R^3$ and $R^4$ preferably have those meanings, which have already been mentioned as preferred for these radicals. M preferably represents lithium, sodium or potassium.

The following compounds may be mentioned as examples of carbonyl compounds of the formula (IV):
Ethyl benzenesulfonyl acetate sodium salt,
isopropyl cyanoacetate sodium salt,
methyl cyanoacetate sodium salt,
ethyl cyanoacetate sodium salt,
ethyl cyanoacetate potassium salt,
ethyl benzoylacetate sodium salt,
5-(4-chlorophenyl)-cyclohexane-1,3-dione sodium salt,
benzoylacetonitrile sodium salt and so on.

The carbonyl compounds of the formula (I) are known or can be prepared by known processes. Thus, they can be synthesized by reacting methylene compounds of the formula

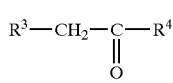 (VII)

in which
R$^3$ and R$^4$ have the above-mentioned meanings,
with strong bases selected from lithium hydride, sodium hydride, potassium hydride, potassium tert-butoxide, sodium methoxide and so on.

The methylene compounds of the formula (VIII) are known or can be prepared by known processes (see EP-A 0 133 349).

Formula (V) provides a general definition of the isothiazolecarboxylic acid derivatives, which are required as starting materials for carrying out process (c) according to the invention. In this formula, R$^c$ preferably represents methyl or ethyl.

The following compounds may be mentioned as examples of isothiazolecarboxylic acid derivatives of the formula (V):
Methyl 3,4-dichloro-5-isothiazolecarboxylate,
ethyl 3,4-dichloro-5-isothiazolecarboxylate.

The isothiazolecarboxylic acid derivatives of the formula (V) are known or can be prepared according to known processes (see JP-A 59 024-1933).

Formula (VI) provides a general definition of the ketones, which are required as reaction components for carrying out process (c) according to the invention. In this formula, R$^5$ preferably has those meanings, which have already been mentioned as preferred for this radical.

The following compounds may be mentioned as examples of ketones of the formula (VI):
Acetophenone,
3-methylacetophenone,
4-methoxyacetophenone,
4-chloroacetophenone,
2-acetylpyridine,
3-acetyl-2,5-dimethylthiophene,
2-acetylthiazole,
2-acetyl-1-methylpyrrole,
4-nitroacetophenone,
2-chloro-4-trifluoromethylacetophenone and so on.

The ketones of the formula (VI) are known or can be prepared by known processes [see Synthetic Communications Vol. 10, 221 (1980)].

Formula (I') provides a general definition of the isothiazole derivatives, which are required as starting materials for carrying out process (d) according to the invention. In this formula, X preferably represents hydrogen, fluoro, chloro or bromo, and R$^d$ preferably represents methyl or ethyl.

The following compound may be mentioned as an example of an isothiazole derivative of the formula (I'):
1-(3,4-Dichloro-5-isothiazolyl)-3-(4-ethoxymethoxy phenyl)-1,3-propanedione.

The isothiazole derivatives of the formula (I') are compounds according to the invention and can be prepared according to processes (a) to (c).

Suitable diluents for conducting process (a) according to the invention are all customary inert organic solvents and water. The following can preferably be used: Water; aliphatic, alicyclic and aromatic hydrocarbons (which may optionally be chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM) etc.; ketones, for example, acetone, methyl ethyl ketone (MEK), methyl isopropyl ketone, methyl isobutyl ketone (MIBK) etc.; nitriles, for example, acetonitrile, propionitrile, acrylonitrile etc.; alcohols, for example, methanol, ethanol, isopropanol butanol, ethylene glycol etc.; esters, for example, ethyl acetate, amyl acetate etc.; acid amides, for example, dimethylformamide (DMF), dimethylacetamide (DMA), N-methylpyrrolidone, 1,3-dimethyl-2-imidazolidinone, hexamethylphosphoric triamide (HMPA) etc.; sulfones and sulfoxides, for example, dimethyl sulfoxide (DMSO), sulfolane etc.; as well as bases, for example, pyridine etc.

Suitable acid-binding agents for conducting process (a) according to the invention are all customary inorganic or organic bases. The following can preferably be used: Inorganic bases, for example, hydrides, hydroxides, carbonates, bicarbonates etc. of alkali metals or alkaline earth metals, for example, sodium hydride, lithium hydride, sodium hydrogen carbonate, potassium hydrogen carbonate, sodium carbonate, potassium carbonate, lithium hydroxide, sodium hydroxide, potassium hydroxide, calcium hydroxide etc.; inorganic alkali metal amides, for example, lithium amid, sodium amide, potassium amide etc.; organic bases, for example, alcoholates, tertiary amines, dialkylaminoanilines and pyridines, for example, triethylamine, 1,1,4,4-tetramethylethylenediamine (TMEDA), N,N-diethylaniline, N,N-diethylaniline, pyridine, 4-dimethylaminopyridine (DMAP), 1,4-diazabicyclo[2,2,2]octane (DABCO), 1,8-diazabicyclo[5,4,0]undec-7-ent (DBU) etc.; organolithium compounds, for example, methyl lithium, n-butyl lithium, sec-butyl lithium, tert-butyl lithium, phenyl lithium, dimethyl copper lithium, lithium diisopropylamide, lithium cyclohexylisopropylamide, lithium dicyclohexylamide, n-butyl lithium-DABCO, n-butyl lithium-DBU, n-butyl lithium-TMEDA etc.

When carrying out process (a) according to the invention, the reaction temperatures can be varied within a substantially wide range. The reaction is generally carried out at a temperature between about −78° C. and about +100° C., preferably between about −10° C. and about +50° C.

Process (a) according to the invention is generally carried out under atmospheric pressure but, if desired, can also be carried out under elevated or reduced pressure.

When carrying out process (a) according to the invention, in general 1 mole of 3,4-dichloro-isothiazole-5-carbonyl chloride of the formula (II) is reacted with 1 to 1.2 moles of a sulfonylamino compound of the formula (III) in the presence of a diluent, such as N,N-dimethylformamide, and in the presence of an acid-binding agent, such as sodium hydride.

Suitable diluents for conducting process (b) according to the invention are all customary inert organic solvents and water. The following can preferably be used: water; aliphatic, alicyclic and aromatic hydrocarbons (which may optionally be chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM) etc.; ketones, for example, acetone, methyl ethyl ketone (MEK), methyl isopropyl ketone, methyl isobutyl ketone (MIBK) etc.; nitriles, for example, acetonitrile, propionitrile, acrylonitrile etc.; alcohols, for example, methanol, ethanol isopropanol, butanol, ethylene glycol etc.; esters, for example, ethyl acetate, amyl acetate etc.; acid amides, for example, dimethylformamide (DMF), dimethylacetamide (DMA), N-methylpyrrolidone, 1,3-dimethyl-2-imidazolidinone, hexamethylphosphoric triamide (HMPA) etc.; sulfones and sulfoxides, for example, dimethyl sulfoxide (DMSO), sulfolane etc., as well as bases, such as pyridine etc.

Suitable acid-binding agents for conducting process (b) according to the invention are all customary inorganic and organic bases. The following can preferably be used: Inorganic bases, such as, hydrides, hydroxides, carbonates, bicarbonates etc. of alkali metals and alkaline earth metals, for example, sodium hydride, lithium hydride, sodium hydrogen carbonate, potassium hydrogen carbonate, sodium carbonate, potassium carbonate, lithium hydroxide, sodium hydroxide, potassium hydroxide, calcium hydroxide etc.; inorganic alkali metal amides, for example, lithium amide, sodium amide, potassium amide etc.; organic bases, such as, alcoholates, tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-diethylaminopyridine (DMAP), 1,4-diazabicyclo[2,2,2]octane (DABCO), 1,8-diazabicyclo[5,4,0]undec-7-ene (DBU) etc.; organolithium compounds, for example, methyl lithium, n-butyl lithium, sec-butyl lithium, tert-butyl lithium, phenyl lithium, dimethyl copper lithium, lithium diisopropylamide, lithium cyclohexylisopropylamide, lithium dicyclohexylamide n-butyl lithium-DABCO, n-butyl lithium-DBU, n-butyl lithium-TMEDA etc.

When carrying out process (b) according to the invention, the reaction temperatures can be varied within a substantially wide range. The reaction is generally carried out at a temperature between about −78° C. and about +100° C., preferably between about −10° C. and about +50° C.

Process (b) according to the invention is generally carried out under atmospheric pressure but, if desired, can also be carried out under elevated or reduced pressure.

When carrying out process (b) according to the invention, in general 1 mole of 3,4-dichloro-isothiazole-5-carbonylchloride of the formula (II) is reacted with 1 to 12 moles of a carbonyl compound of the formula (IV) in the presence of a diluent, such as tetrahydrofuran.

Suitable diluents for conducting process (c) according to the invention are all customary organic solvents and water. The following can preferably be used: Water; aliphatic, alicyclic and aromatic hydrocarbons (which may optionally be chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM) etc.; ketones, for example, acetone, methyl ethyl ketone (MEK), methyl isopropyl ketone, methyl isobutyl ketone (MIBK) etc.; nitriles, for example, acetonitrile, propionitrile, acrylonitrile etc.; alcohols, for example, methanol, ethanol, isopropanol, butanol, ethylene glycol etc.; esters, for example, ethyl acetate, amyl acetate etc.; acid amides, for example, dimethylformamide (DMF), dimethylacetamide (DMA), N-methylpyrrolidone, 1,3-dimethyl-2-imidazolidinone, hexamethylphosphoric triamide (HMPA) etc.; sulfones and sulfoxides, for example, dimethyl sulfoxide (DMSO), sulfolane etc. as well as bases, for example, pyridine etc.

Suitable acid-binding agents for conducting process (c) according to the invention are all customary inorganic and organic bases. The following can preferably be used: Inorganic bases, for example, hydrides, hydroxides etc. of alkali metals or alkaline earth metals, for example, sodium hydride, lithium hydride, lithium hydroxide, sodium hydroxide, potassium hydroxide, calcium hydroxide etc.; inorganic alkali metal amides, for example, lithium amide, sodium amide, potassium amide etc.; as organic bases, for example, alcoholates, tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-diethylaminopyridine (DMAP), 1,4-diazabicyclo[2,2,2]octane (DABCO), 1,8-diazabicyclo[5,4,0]undec-7-ene (DBU) etc.; organolithium compounds, for example, methyl lithium, n-butyl lithium, sec-butyl lithium, tert-butyl lithium, phenyl lithium, dimethyl copper lithium, lithium diisopropylamide, lithium cyclohexylisopropylamide, lithium dicyclohexylamide, n-butyl lithium-DABCO, n-butyl lithium-DBU, n-butyl lithium-TMEDA etc.

When carrying our process (c) according to the invention, the reaction temperatures can be varied within a substantially wide range. The reaction is generally carried out at a temperature between about −78° C. and about +100° C., preferably between about −10° C. and about +50° C.

Process (c) according to the invention is generally carried out under atmospheric pressure but, if desired, can also be carried out under elevated or reduced pressure.

When caring out process (c) according to the invention, in general 1 mole of an isothiazolecarboxylic acid derivative of the formula (V) is reacted with 1 to 1.5 moles of a ketone of the formula (VI) in the presence of a diluent, such as tetrahydrofuran, and in the presence of an acid-binding agent, such as sodium hydride.

Suitable diluents for conducting process (d) according to the invention are water as well as customary inert organic solvents. The following can preferably be used: Water, ethers, for example, ethyl ether, methyl ethyl ether, isopropyl ether, butyl ether, dioxane, dimethoxyethane (DME), tetrahydrofuran (THF), diethylene glycol dimethyl ether (DGM) etc.; ketones, for example, acetone, methyl ethyl ketone (MEK), methyl isopropyl ketone, methyl isobutyl ketone (MIBK) etc.; nitriles, for example, acetonitrile, propionitrile, acrylonitrile etc.; alcohols, for example, methanol, ethanol, isopropanol, butanol, ethylene glycol etc.; esters, for example, ethyl acetate, amyl acetate etc.; acid amides, for example, dimethylformamide (DMF), dimethylacetamide (DMA), N-methylpyrrolidone, 1,3-dimethyl-2-imidazolidinone, hexamethylphosphoric trimide (HMPA) etc.; sulfones and sulfoxides, for example, dimethyl sulfoxide (DMSO), sulfolane etc., as well as bases, for example, pyridine etc.

Suitable catalysts for conducting process (d) according to the invention are all customary acid catalysts. Preferred catalysts of this type are mineral acids, for example, hydrochloric acid, sulfuric acid, nitric acid, hydrobromic acid, sodium hydrogen sulfite etc.; organic acids, for example, formic acid, acetic acid, trifluoroacetic acid, propionic acid, methanesulfonic acid, benzenesulfonic acid, p-toluenesulfonic acid etc.; organic amine hydrochlorides, for example, pyridine hydrochloride, triethylamine hydrochloride etc., amine sulfonates, for example, pyridine p-toluenesulfonate, triethylamine p-toluenesulfonate etc.

When carrying our process (d) according to the invention, the reaction temperatures can be varied within a substantially wide range. The reaction is generally carried out at a temperature between about −20° C. and about +150° C., preferably between about 0° C. and about +150° C.

Process (d) according to the invention is generally carried out under atmospheric pressure but, if desired, can also be carried out under elevated pressure.

When carrying out process (d) according to the invention, in general 1 mole of isothiazole derivative of the formula (I') is treated with 1 to 20 moles of an acid catalyst, such as concentrated hydrochloric acid, and in the presence of a diluent, such as a mixture of isopropanol and tetrahydrofuran.

The compounds of the formula (I) prepared by the above-mentioned processes can in each case be isolated from the reaction mixtures by customary procedures and can be purified by known methods, such as crystallization, chromatography etc.

The compounds according to the present invention exhibit a strong microbicidal activity. Thus, they can be used for combating undesired microorganisms, such as phytopathogenic fungi and bacteriae, in agriculture and horticulture. The compounds are suitable for the direct control of undesired microorganisms as well as for generating resistance in plants against attack by undesired plant pathogens.

Resistance-inducing substances in the present context are to be understood as those substances which are capable of stimulating the defence system of plants such that the treated plants, when subsequently inoculated with undesirable microorganisms, display substantial resistance to these microorganisms.

Undesirable microorganisms in the present case are to be understood as phytopathogenic fungi and bacteriae. The substances according to the invention can thus be employed to generate resistance in plants against attack by the harmful organisms mentioned within a certain period of time after the treatment. The period of time within which resistance is brought about in general extends from 1 to 10 days, preferably 1 to 7 days, after treatment of the plants with the active compounds.

Generally, the compounds according to the invention can be used as fungicides for combating phytopathogenic fungi, such as Plasmodiophoromycetes, Oomycetes, Chytridiomycetes, Zygomycetes, Ascomycetes, Basidiomycetes and Deuteromycetes, and can also be used as bactericides for combating bacteriae, such as Pseudomonadaceae, Rhizobiaceae, Enterobacteriaceae, Corynebacteriaccae, Streptomycetaceae, Proteobacteriae and Gram-positive groups.

The compounds according to the present invention are particularly suitable for causing resistance against infection of plants by plant pathogens, such as *Pyricularia oryzae*, Phythophthora infestans etc.

The good toleration, by plants, of the active compounds, at the concentrations required for combating plants diseases, permits treatment of above-ground parts of plants, of vegetative propagation stock and seeds, and of the soil.

The compounds according to the present invention have a low toxicity against warm-blooded animals and therefore can be used safely.

The active compounds can be converted into the customary formulations, such as solutions, emulsions, wettable powders, suspensions, powders, foams, pastes, granules, tablets, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons such as xylene, toluene or alkyl naphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl-isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolings, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifing and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products.

Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuff, such as alizarin dyestuffs, azo dyestaffs or metal phthalocyanine dyestuffs, and trace nutrients, such as salts of iron, manganese, boron, copper, cobalt, molybdenum and zinc.

The formulations in general contain from 0.1 to 95 per cent by weight of active compound, preferably from 0.5 to 90 per cent by weight The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

In many cases, synergistic effects are achieved, i.e. the activity of the mixture exceeds the activity of the individual components.

Examples of co-components in mixtures are the following compounds:

Fungicides:
- aldimorph, ampropylfos, ampropylfos potassium, andoprim, anilazine, azaconazole, azoxystrobin,
- benalaxyl, benodanil benomyl, benzamacril, benzamacril-isobutyl, bialaphos, binapacryl, biphenyl, bitertanol, blasticidin-S, bromuconazole, bupirimate, buthiobate,
- calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, carpropamide,
- debacarb, dichlorophen, diclobutrazole, diclofluanid, diclomezine, dicloran, diethofencarb, difenoconazole, dimethirimol dimethomorph, diniconazole, diniconazole-M, dinocap, diphenylamine, dipyrithione, ditalimfos, dithianon, dodemorph, dodine, drazoxolon,
- edifenphos, epoxiconazole, etaconazole, ethirimol, etridiazole,
- famoxadon, fenapanil, fenariimol, fenbuconazole, fenfuram, fenitropan, fenpiclonil fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl furametpyr, furcarbonil, furconazole, furconazole-cis, furmecyclox, fenhexamide,
- guazatine,
- hexachlorobenzene, hexaconazole, hymexazole
- imazalil, imibenconazole, iminoctadine, iminoctadine albesilate, iminoctadine triacetate, iodocarb, ipconazole, iprobenfos (IBP), iprodione, irumamycin, isoprothiolane, isovaledione, iprovalicarb,
- kasugamycin, kresoxim-methyl, copper preparations, such as: copper hydroxide, copper naphthenate, copper oxychloride, copper sulphate, copper oxide, oxine-copper and Bordeaux mixture,
- mancopper, mancozeb, maneb, meferimzone, mepanipyrim, mepronil metalaxyl metconazole, methasulfocarb, methiroxam, metiram, metomeclam, metslfovax, mildiomycin, myclobutanil, myclozolin,
- nickel dimethyldithiocarbamate, nitrothal-isopropyl, nuarimol
- ofurace, oxadixyl, oxamocarb, oxolinic acid, oxycarboxim, oxyfenthiin,
- paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
- quinconazole, quintozene (PCNB), quinoxyfen,
- sulphur and sulphur preparations, spiroxamine,
- tebuconazole, tecloftalam, tecnazene, tetcyclacis, tetraconazole, thiabendazole, thicyofen, thifluzde, thiophanate-methyl, thiram, tioxymid, tolclofos-methyl, tolylifluanid, triadimefon, triadimenol, triazbutil, triazoxide, trichlamide, tricyclazole, tridemorph, triflunizole, triforine, triticonazole, trifoxystrobin,
- uniconazole,
- validamycin A, vinclozolin, viniconazole,
- zarilamide, zineb, ziram and also
- Dagger G,
- OK-8705,
- OK-8801,
- α-(1,1-dimethylethyl)-β-(2-phenoxyethyl)-1H-1,2,4-triazole-1-ethanol,
- α-(2,4-dichlorophenyl)-β-fluoro-β-propyl-1H-1,2,4-triazole-1-ethanol,
- α-(2,4-dichlorophenyl)-β-methoxy-α-methyl-1H-1,2,4-triazole-1-ethanol,
- α-(5-methyl-1,3-dioxan-5-yl)-β-[[4-(trifluoromethyl)-phenyl]-methylene]-1H-1,2,4-triazole-1-ethanol,
- (5RS,6RS)-6-hydroxy-2,2,7,7-tetramethyl-5-(1H-1,2,4-triazol-1-yl)-3-octanone,
- (E)-α-(methoxyimino)-N-methyl-2-phenoxy-phenylacetamide,
- 1-(2,4-dichlorophenyl)-2-(1H-1,2,4-triazol-1-yl)-ethanone O-phenylmethyl)-oxime,
- 1-(2-methyl-1-naphthalenyl)-1H-pyrrol-2,5-dione,
- 1-(3,5-dichlorophenyl)-3-(2-propenyl)-2,5-pyrrolidinedione,
- 1-[(diiodomethyl)-sulphonyl]-4-methyl-benzene,
- 1-[[2-(2,4-dichlorophenyl)-1,3-dioxolan-2-yl]-methyl]-1H-imidazole,
- 1-[[2-(4-chlorophenyl)-3-phenyloxiranyl]-methyl]-1H-1,2,4-triazole,
- 1-[1-[2-[(2,4-dichlorophenyl)-methoxy]-phenyl]-ethenyl]-1H-imidazole,
- 1-methyl-5-nonyl-2-(phenylmethyl)-3-pyrrolidinole,
- 2',6'-dibromo-2-methyl-4'-trifluoromethoxy-4'-trifluoromethyl-1,3-thiazole-5-carboxanilide,
- 2,6-dichloro-5-(methylthio)-4-pyrimidinyl thiocyanate,
- 2,6-dichloro-N-(4-trifluoromethylbenzyl)-benzamide,
- 2,6-dichloro-N-[[4-(trifluoromethyl)-phenyl]-methyl]-benzamide,
- 2-(2,3,3-triodo-2-propenyl)-2H-tetrazole,
- 2-[(1-methylethyl)sulphonyl]-5-(trichloromethyl)-1,3,4-thiadiazole,
- 2-[[6-deoxy-4-O-(4-O-methyl-β-D-glycopyranosyl)-α-D-glucopyranosyl]-amino-]-4-methoxy-1H-pyrrolo[2,3-d]pyrimidine-5-carbonitrile,
- 2-aminobutane,
- 2-bromo-2-(bromomethyl)-pentanedinitrile,
- 2-chloro-N-(2,3-dihydro-1,1,3-trimethyl-1H-inden-4-yl)-3-pyridinecarboxamide,
- 2-chloro-N-(2,6-dimethylphenyl)-N-(isothiocyanatomethyl)-acetamide, 2-phenylphenol (OPP),
3,4-dichloro-1-[4-(difluoromethoxy)-phenyl]-1H-pyrrol-2,5-dione,
3,5-dichloro-N-[cyano[(1-methyl-2-propinyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidaole-1-sulphonamide,
4-methyl-tetrazolo[1,5-a]quinazolin-5(4H)-one,
8-hydroxyquinoline sulphate,
9H-xanthene-2-[(phenylamio)-carbonyl]-9-carboxylic hydrazide,
bis-(1-methylethyl)-3-methyl-4-[(3-methylbenzoyl)-oxy] 2,5-thiophenedicarboxylate,
cis-1-(4-chlorophenyl)-2-1H-1,2,4-triazol-1-yl)-cycloheptanol,
cis-4-[3-[4-(1,1-dimethylpropyl)-phenyl-2-methylpropyl]-2,6-dimethylmorpholinehydrochloride,
ethyl[(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/acaricides/nematicides:
abamectin, acephate, acetamiprid, acrinathnin, alanycarb, aldicarb, aldoxycarb, alpha-cypermethrin, alphamethin amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis,* baculoviruses, *Beauveria bassiana, Beauveria tenella*, bendiocarb, benfiracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoat, dimethylvinphos, diofenolan, disulfoton, docusat-sodium, dofenapyn,
eflusilanate, emamectin, empenthrin, endosulfan, Entomopfthora spp., esfenvalerate, ethiofencarb, ethion, ethoprophos, etofenprox, etoxazole, etrimphos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, isazophos, isofenphos, isoxathion, ivermectin,
lambda-cyhalothrin, lufenumon,
malathion, mecarbam, metaldehyde, methamidophos, *Metharhizium anisopliae, Metharhiziun flavoviride*, methidathion, methiocarb, methomyl, methoxyfenozide, metolcarb, metoxadiazone, mevinphos, milbemectin, monocrotophos,
naled, nitenpyram, nithiazine, novaluron, nuclear polyhedrosis viruses,
omethoat, oxamyl, oxydemethon M,
*Paecilomyces fumosoroseus*, parathion A, parathion M, permethlrin, phenthoat, phorat, phosalone, phosmet, phosphamidon, phoxim, pirimicarb, pirimiphos A, pirimiphos M, profenofos, promecarb, propoxur, prothiofos, prothoat, pymaetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, thiacloprid,
vamidothion, vaniliprole, *Verticillium lecanii,*

YI 5302,
zeta-cypermethrin, zolaprofos,
(1R-cis)-[5-(phenylmethyl)-3-furanyl]-methyl-3-[(dihydro-2-oxo-3(2H)-furanylidene)-methyl]2,2-dimethylcyclopropanecarboxylate,
(3-phenoxyphenyl)-methyl 2,2,3,3-tetramethylcyclopropanecarboxylate,
1-[(2-chloro-5-thiazolyl)methyl]tetrahydro-3,5-dimethyl-N-nitro-1,3,5-thiazine-2(1H)-imine,
2-(2-chloro-6-fluorophenyl)-4-[4-(1,1-dimethylethyl)phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4chloro-2-(2-chloro-2-methylpropyl)-5-[(6-iodo-3-pyridinyl)methoxy]-3(2H)pyridazinone,
4-chloro-5-[(6-chloro-3-pyrdinyl)methoxy]-2-(3,4-dichlorophenyl)-3(2M-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyrdinyl)methyl]-2-thiazolidinylidene]-cyananide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N"-nitro-guanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl [2-dipropylamino)-2-oxoethyl]-ethylphosphoramidothioate.

The active compounds can be used as such or in the form of their formulations or the use forms prepared therefrom by further dilution, such as ready-to-use solutions, emulsions, suspensions, powders, tablets, pastes, microcapsules and granules. They are used in the customary manner, for example by watering, immersion, spraying, atomising, misting, vaporizing, injecting, forming a slurry, brushing on, dusting, scattering, dry dressing, moist dressing, wet dressing, slurry dressing or encrusting.

In the treatment of parts of plants, the active compounds concentration in the use forms can be varied within a substantial range. They are, in general, from 1 to 0.0001% by weight, preferably from 0.5 and 0.001%.

For the treatment of seed, amounts of active compound of 0.001 to 50 g, especially 0.01 to 10 g, are generally employed per kilogram of seed.

For the treatment of soil, active compound concentrations, at the point of action, of 0.00001 to 0.1% by weight, especially of 0.0001 to 0.02%, are generally employed As already mentioned above, all plants and parts of plants can be treated according to the invention. In a preferred embodiment naturally occurring plant species and plant varieties or those obtained by conventional biological breeding methods, such as crossbreeding or protoplast fusion as well as parts of such plants are treated. In an additional preferred embodiment transgenic plants and plant varieties which have been obtained by genetic engineering methods, possibly in combination with conventional methods (genetically modified organisms) and parts of such plants are treated. The term "parts" or "parts of plants" or "plant parts" is explained above.

According to the invention plants of the plant varieties commercially available or used at any particular time are very preferably treated. Plant varieties are understood to be plants with specific properties ("traits") which have been obtained both by conventional breeding, by mutagenesis or by recombinant DNA techniques. They can be varieties, biotypes or genotypes.

Depending on the species or varieties of plants, their location and growth conditions (the types of soil, climate, vegetation period and feed concerned), superadditive ("synergistic") effects can occur as a result of the treatment according to the invention. Effects such as for example reduced application rates and/or broadening of the activity spectra and/or increased activity of the compounds and compositions usable according to the invention, improved plant growth, increased tolerance of high or low temperatures, increased tolerance of dry conditions or water or ground salt contents, increased flowering capacity, facilitated harvesting, acceleration of maturity, increased crop yields, higher quality and/or increased nutritional value of the harvested crops and increased storing quality and/or processibility of the harvested crops are possible, which are greater than those actually expected.

Preferred transgenic plants or plant varieties (obtained by genetic engineering) to be treated according to the invention include all plants which as a result of the genetic modification concerned have received genetic material which provides them with particularly advantageous valuable properties ("traits"). Examples of such properties are improved plant growth, increased tolerance of high or low temperatures, increased tolerance of dry conditions or water or ground salt contents, increased flowering capacity, facilitated harvesting, acceleration of maturity, increased crop yields, higher quality and/or increased nutritional value of the harvested crops and increased storing quality and/or processibility of the harvested crops. Additional and particularly noteworthy examples of such properties are increased resistance of the plants to animal and microbial pests, such as to insects, mites, phytopathogenic fungi, bacteria and/or viruses as well as increased tolerance by the plants of certain herbicidal active compounds. Examples which may be mentioned of transgenic plants are the important crop plants such as cereals (wheat and rice), corn, soybeans, potatoes, cotton, rape and fruit plants (producing apples, pears, citrus fruits and grapes), the crop plants corn, soybeans, potatoes, cotton and rape being particularly noteworthy. Particularly significant properties ("traits") are increased resistance of the plants to insects due to the toxins forming in the plants, and in particular those which are produced in the plants (hereinafter referred to as "Bt plants") by the genetic material obtained from Bacillus Thuringiensis (e.g. by the genes CryIA(a), CryIA(b), CryIA(c), CryIIA, CryIIIB2, Cry9c Cry2Ab, Cry3Bb and CryIF and combinations thereof). Particularly significant properties ("traits") are the increased resistance of plants to fungi, bacteria and viruses due to systemically acquired resistance (SAR), systemin, phytoalexins, elicitors and resistance genes and correspondingly expressed proteins and toxins. Particularly significant properties ("traits") are also increased tolerance by the plants of certain herbicidal active compounds, such as for example imidazolinones, sulphonylureas, glyphosate or phosphinotricine (e.g. the "PAT" gene). The corresponding genes imparting the required properties ("traits"). can also occur in the transgenic plants in combination with each other. Examples which may be mentioned of "Bt plants" are varieties of corn, cotton, soybeans and potatoes which are sold under the trade names YIELD GARD® (e.g. corn, cotton, soybeans), KnockOut® (e.g. corn), StarLink® (e.g. corn), Bollgard® (cotton), Nucotn® (cotton) and NewLeaf® (potatoes). Examples which may be mentioned of herbicide-tolerant plants are varieties of corn, cotton and soybeans which are sold under the trade names Roundup Ready® (tolerance of glyphosate, e.g. corn, cotton, soybeans), Liberty Link® (tolerance of phosphinotricine, e.g. rape), IMI® (tolerance of imidazolinones) and STS® (tolerance of sulphonylureas, e.g. corn). Herbicide-resistant plants (bred for herbicide tolerance in the conventional manner) which may be mentioned are also the varieties (e.g. corn) sold under the name Clearfield®. The above statements do of course also apply to any plant varieties which may be developed in the future or launched onto the market in the future and which have the genetic properties ("traits") described above or developed in the future.

According to the invention the abovementioned plants can be particularly advantageously treated with the compounds of the general formula I or the active compound mixtures according to the invention. The preferred ranges mentioned above for the active compounds or mixtures also apply to the treatment of these plants. Particularly advantageous is the treatment of plants with the compounds or mixtures specifically listed in the present text.

Then the present invention will be described more specifically by the following examples. However, the present invention should not be restricted to them in any way.

SYNTHESIS EXAMPLE 1

Compound No. Ia-68

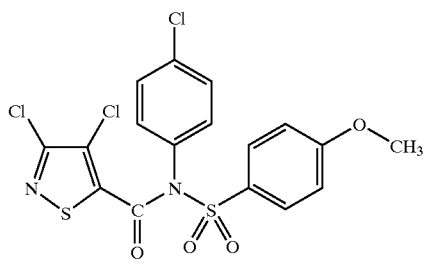

Process (a):

To a solution of N-(4-chlorophenyl)-4-methoxybenzenesulfonamide (1.98 g) in unhydrous N,N-dimethylformamide (20 ml) 60% sodium hydride (0.24 g) was added at room temperature. After stirring the reaction mixture at the same temperature for 1 hour, a solution of 3,4-dichloro-5-isothiazolecarbonyl chloride (1.1 g) in unhydrous N,N-dimethylformamide (10 ml) was added thereto dropwise. After finishing the addition, the reaction mixture was stirred at room temperature for 18 hours and poured into water. The mixture was extracted with ethyl acetate and the organic phase was washed with water and dried with unhydrous sodium sulfate. The crude product obtained by distilling off the solvent under reduced pressure was recrystallized from ethanol to obtain N-(3,4-dichloro-5-isothiazolecarbonyl)-N-(4-chlorophenyl)-4-methoxybenzenesulfonamide (0.89 g). mp 154–158° C.

SYNTHESIS EXAMPLE 2

Compound No. Ie-1

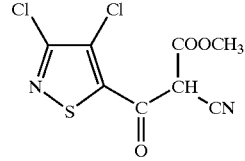

Process (b):

To a solution of methyl cyanoacetate (1.98 g) in unhydrous tetrahydrofuran (20 ml) 60% sodium hydride (1.6 g) was added at a temperature below 10° C. To the reaction mixture a solution of 3,4-dichloro-5-isothiazolecarbonyl chloride (4.30 g) in unhydrous tetrahydrofuran (15 ml) was added dropwise at the same temperature. After finishing the addition, the reaction mixture was stirred at room temperature for 2 hours and 1N-aqueous hydrochloric acid (10 ml) was added. After extraction with ethyl acetate and drying the organic phase with unhydrous sodium sulfate, the solvent was distilled off under reduced pressure to obtain methyl 2-cyano-3-(3,4-dichloro-5-isothiazolyl)-3-oxopropanoate (4.7 g) as pale yellow crystals. mp 119–122° C.

SYNTHESIS EXAMPLE 3

Compound No. Ic-146

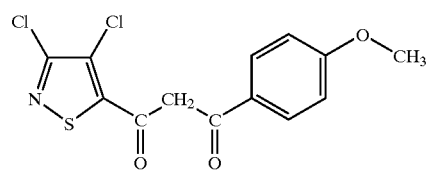

Process (c):

To a solution of 4-methoxyacetophenone (0.75 g) and methyl 3,4-dichloro-5-isothiazolecarboxylate (1.70 g) in diethyl ether (30 ml) a methanol solution containing 28% sodium methoxide (1.4 g) was added dropwise while stirring under ice cooling. After stirring at room temperature for 24 hours, the reaction mixture was poured into ice and 1N-aqueous hydrochloric acid (10 ml) was added thereto. After the organic layer was separated, washed with water and dried with unhydrous sodium sulfate, the solvent was distilled off under reduced pressure. The residue was purified by silica gel column chromatography (eluent hexane:ethyl acetate=85:15) to obtain 1-(3,4-dichloro-5-isothiazolyl)-3-(4-methoxyphenyl)-1,3-propaniedione (0.85 g) as pale yellow crystals. mp 138–139° C.

SYNTHESIS EXAMPLE 4

Compound No. Ic-148

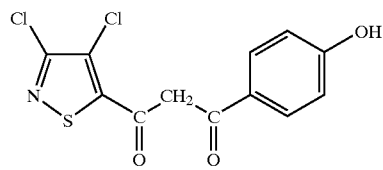

Process (d):

To a solution of 1-(3,4-dichloro-5-isothiazolyl)-3-(4-ethoxymethoxyphenyl)-1,3-propanedione (1.20 g) in a mixture of isopropanol (20 ml) and tetrahydrofuran (20 ml) concentrated hydrochloric acid (3.40 g) was added at room temperature and the mixture was stirred for 12 hours. After distilling off the solvent under reduced pressure, the residue was purified by silica gel column chromatography (eluent hexane:ethyl acetate=50:50) to obtain 1-(3,4-dichloro-5-isothiazolyl)-3-(4-hydroxyphenyl)-1,3-propanedione (0.90 g). mp 224–227° C.

The compounds obtained in the similar manner as the above-mentioned Synthesis Examples 1–4 are shown, together with the compounds synthesized in Synthesis Examples 1–4, in the following Tables 1–5.

The compounds of the formula (I) are represented in Table 1 by the formula

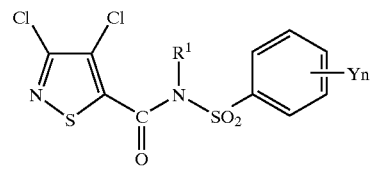
(Ia)

in Table 2 by the formula

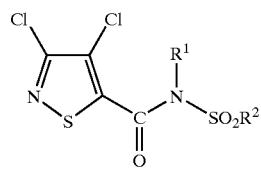
(Ib)

in Table 3 by the formula

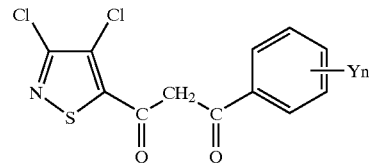
(Ic)

in Table 4 by the formula

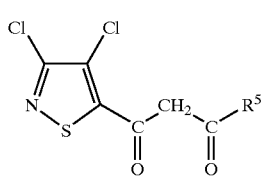
(Id)

and Table 5 by the formula

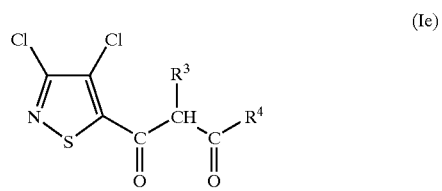
(Ie)

TABLE 1

(Ia)

| Compound No. | $R^1$ | $Y_n$ | mp (° C.) or $n_D^{20}$ |
|---|---|---|---|
| Ia-1 | $CH_3$ | 2- phenyl | 1.6139 |
| Ia-2 | H | 2,3,4-$Cl_3$ | |
| Ia-3 | H | 2,3,4-$F_3$ | |
| Ia-4 | H | 2,3-$Cl_2$ | |
| Ia-5 | H | 2,4,5-$Cl_3$ | |
| Ia-6 | H | 2,4-$Cl_2$, 5-$CH_3$ | |
| Ia-7 | $O_2N$-phenyl | 2,4-$Cl_2$ | |
| Ia-8 | 3-$NO_2$-phenyl | 2,4-$Cl_2$ | |
| Ia-9 | 4-$NO_2$-phenyl | 2,4-$Cl_2$ | |
| Ia-10 | $CH(C_3H_7\text{-iso})CO_2CH_3$ | 2,4-$Cl_2$ | 1.5751 |
| Ia-11 | $CH_3$ | 2,4-$Cl_2$ | |
| Ia-12 | H | 2,4-$Cl_2$ | |
| Ia-13 | H | 2,4-$F_2$ | |
| Ia-14 | H | 2,5-$(CH_3)_2$, 4-Cl | |
| Ia-15 | H | 2,5-$(OCH_3)_2$ | |
| Ia-16 | H | 2,5-$Cl_2$ | |
| Ia-17 | H | 2,5-$F_2$, 4-Br | |
| Ia-18 | H | 2-Br, 5-$OCH_3$ | |
| Ia-19 | H | 2-Br | |
| Ia-20 | H | 2- phenyl | |
| Ia-21 | H | 2-$CF_3$ | |
| Ia-22 | H | 2-$CH_3$, 3-Cl | |
| Ia-23 | H | 2-$CH_3$, 4-Br | |
| Ia-24 | H | 2-$CH_3$, 5-F | |
| Ia-25 | H | 2-Cl, 4-$CF_3$ | |
| Ia-26 | H | 2-Cl, 4-F | |

TABLE 1-continued

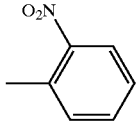

(Ia)

| Compound No. | R¹ | Yₙ | mp (° C.) or $n_D^{20}$ |
|---|---|---|---|
| Ia-27 | H | 2-Cl, 5-CF₃ | |
| Ia-28 | C₃H₇-iso | 2-Cl | |
| Ia-29 | CH₃ | 2-Cl | |
| Ia-30 | H | 2-Cl | |
| Ia-31 | H | 2-CN | |
| Ia-32 | H | 2-F | |
| Ia-33 | CH₃ | 2-NH₂ | 199–201 |
| Ia-34 | 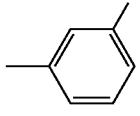 | 2-NO₂ | |
| Ia-35 | 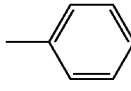 | 2-NO₂ | |
| Ia-36 | 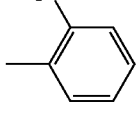 | 2-NO₂ | |
| Ia-37 | CH₃ | 2-NO₂ | 144–145 |
| Ia-38 | H | 2-OCF₃ | |
| Ia-39 | H | 2-OCH₃, 4-CH₃ | |
| Ia-40 | H | 2-OCH₃, 5-Cl | |
| Ia-41 | H | 3,4-(OCH₃)₂ | |
| Ia-42 | H | 3,4-Cl₂ | |
| Ia-43 | H | 3,4-F₂ | |
| Ia-44 | H | 3,5-(CF₃)₂ | |
| Ia-45 | H | 3,5-Cl₂ | |
| Ia-46 | C₃H₇-iso | 3,5-Cl₂ | 102–103 |
| Ia-47 | H | 3-Br | |
| Ia-48 | H | 3-CF₃ | |
| Ia-49 | H | 3-CH₃ | |
| Ia-50 | H | 3-Cl, 4-CH₃ | |
| Ia-51 | H | 3-Cl, 4-F | |
| Ia-52 | 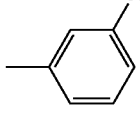 | 3-Cl | |
| Ia-53 | 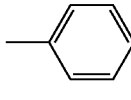 | 3-Cl | |
| Ia-54 | 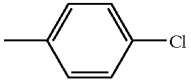 | 3-Cl | |
| Ia-55 | C₃H₇-iso | 3-Cl | |
| Ia-56 | CH₃ | 3-Cl | 98–99 |
| Ia-57 | H | 3-Cl | |
| Ia-58 | CH₂C≡CH | 3-Cl | 75–78 |
| Ia-59 | H | 3-CN | |
| Ia-60 | H | 3-F | |
| Ia-61 | H | 3-NO₂, 4-CH₃ | |
| Ia-62 | C₃H₇-iso | 3-NO₂, 4-Cl | 103–104 |
| Ia-63 | H | 3-NO₂ | |
| Ia-64 | H | 3-OCH₃ | |
| Ia-65 | H | 4-C₃H₇-iso | |
| Ia-66 | H | 4-C₃H₇-n | |
| Ia-67 | H | 4-C₄H₉-n | |
| Ia-68 | 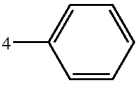 | 4-OCH₃ | 154–158 |
| Ia-69 | H | 4-OC₄F₉-n | |
| Ia-70 | H | 4-C₄H₉-tert | |
| Ia-71 | H | 4-C₅H₁₁-tert | |
| Ia-72 | H | 4-Br | |
| Ia-73 | H | 4-C₂H₅ | |
| Ia-74 | CH₃ | 4-C₆H₅ | 131–132 |
| Ia-75 | H | 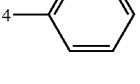 | |
| Ia-76 | C₃H₇-iso | 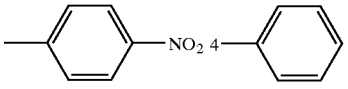 | 96–99 |
| Ia-77 |  | 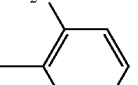 | 197–203 |
| Ia-78 | H | 4-CF₃ | |
| Ia-79 | 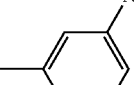 | 4-CH₃ | |
| Ia-80 | 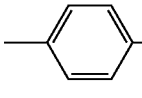 | 4-CH₃ | |
| Ia-81 | 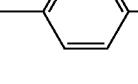 | 4-CH₃ | |
| Ia-82 |  | 4-CH₃ | 151–155 |

TABLE 1-continued

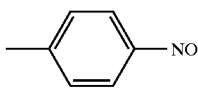

(Ia)

| Compound No. | R¹ | $Y_n$ | mp (° C.) or $n_D^{20}$ |
|---|---|---|---|
| Ia-83 | 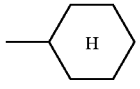 (4-NO₂ phenyl-CH₂) | 4-CH₃ | 226–228 |
| Ia-84 | C₂H₅ | 4-CH₃ | 1.5883 |
| Ia-85 | C₆H₅ | 4-CH₃ | 148–149 |
| Ia-86 | CH₃ | 4-CH₃ | 1.6010 |
| Ia-87 | CO₂C₄H₉-tert | 4-CH₃ | 128–129 |
| Ia-88 | 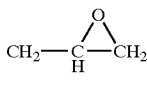 (cyclohexyl-CH₂) | 4-CH₃ | 1.5805 |
| Ia-89 | H | 4-CH₃ | |
| Ia-90 | C₃H₇-iso | 4-CH₃ | |
| Ia-91 | CH₂—CH(O)—CH₂ (glycidyl) | 4-Cl | 114–115 |
| Ia-92 | 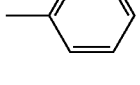 (2-NO₂ benzyl) | 4-Cl | 194–195 |
| Ia-93 | 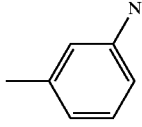 (3-NO₂ benzyl) | 4-Cl | 188–190 |
| Ia-94 | 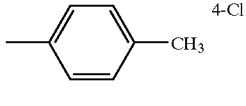 (4-CH₃ benzyl) | 4-Cl | |
| Ia-95 | 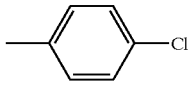 (4-Cl benzyl) | 4-Cl | 143 |
| Ia-96 | 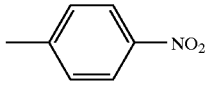 (4-NO₂ benzyl) | 4-Cl | 209–213 |
| Ia-97 | 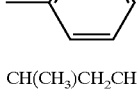 (benzyl) | 4-Cl | 157–158 |
| Ia-98 | CH(CH₃)CH₂CH(CH₃)₂ | 4-Cl | 95–97 |
| Ia-99 | CH₂CH=CH₂ | 4-Cl | 1.5920 |
| Ia-100 | CH₃ | 4-Cl | 86–91 |
| Ia-101 | 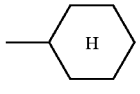 (cyclohexyl-CH₂) | 4-Cl | 127–128 |
| Ia-102 | H | 4-Cl | 93–95 |
| Ia-103 | C₃H₇-iso | 4-Cl | 109–111 |
| Ia-104 | CH₂C≡CH | 4-Cl | |
| Ia-105 | H | 4-CN | |
| Ia-106 | 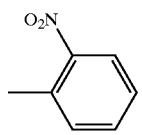 (2-NO₂ benzyl) | 4-CN | |
| Ia-107 | 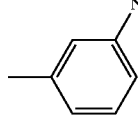 (3-NO₂ benzyl) | 4-CN | |
| Ia-108 | 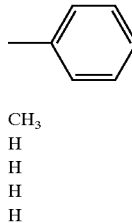 (4-NO₂ benzyl) | 4-CN | |
| Ia-109 | CH₃ | 4-CN | 139–140 |
| Ia-110 | H | 4-F | |
| Ia-111 | H | 4-I | |
| Ia-112 | H | 4-NH₂ | 238–239 |
| Ia-113 | H | 4-NO₂ | |
| Ia-114 | 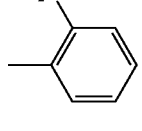 (2-NO₂ benzyl) | 4-NO₂ | |
| Ia-115 | 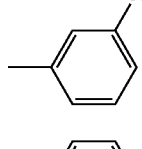 (3-NO₂ benzyl) | 4-NO₂ | |
| Ia-116 | 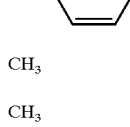 (4-NO₂ benzyl) | 4-NO₂ | |
| Ia-117 | CH₃ | 4-NO₂ | 175–178 |
| Ia-118 | CH₃ | 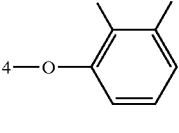 (4—O—(2-CN-6-Cl phenyl)) | 114–115 |
| Ia-119 | H | 4-OCF₃ | |
| Ia-120 | H | 4-OCH₃ | |
| Ia-121 | H | 2,3,4,5,6-F₅ | |

TABLE 1-continued
(Ia)
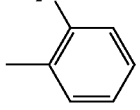
| Compound No. | R¹ | Yₙ | mp (° C.) or $n_D^{20}$ |
|---|---|---|---|
| Ia-122 | 2-O₂N-C₆H₄-CH₂- | — | |
| Ia-123 | 3-O₂N-C₆H₄-CH₂- | — | |
| Ia-124 | 4-CH₃-C₆H₄-CH₂- | — | |
| Ia-125 | 4-Cl-C₆H₄-CH₂- | — | 176–177 |
| Ia-126 | 4-NO₂-C₆H₄-CH₂- | — | |
| Ia-127 | C₆H₅-CH₂- | — | 129–130 |
| Ia-128 | CH₃ | — | 109–110 |
| Ia-129 | H | — | |
| Ia-130 | C₃H₇-iso | — | |
| Ia-131 | C₆H₅-N(CH₃)-CH₂- | — | 181–182 |
| Ia-132 | C₄H₉-n | — | 1.5773 |
TABLE 2
(Ib)
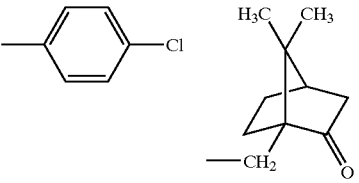
| Compound No. | R¹ | R² | mp (° C.) or $n_D^{20}$ |
|---|---|---|---|
| Ib-1 | 4-Cl-C₆H₄-CH₂- | (CH₂)₃Cl | 114–116 |
| Ib-2 | H | (CH₂)₃Cl | |
| Ib-3 | 4-Cl-C₆H₄-CH₂- | camphor-CH₂- | 66–72 |

TABLE 2-continued
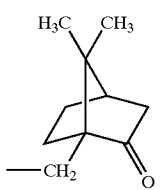
(Ib)
| Compound No. | R¹ | R² | mp (° C.) or $n_D^{20}$ |
|---|---|---|---|
| Ib-4 | H | 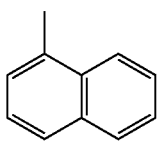 | |
| Ib-5 | H | 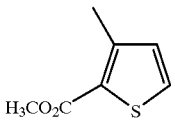 | |
| Ib-6 | CH₃ | 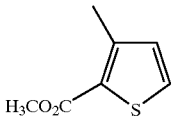 | 123–124 |
| Ib-7 | H | 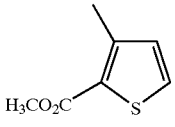 | 167–170 |
| Ib-8 | C₃H₇-iso | 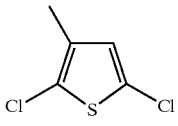 | 124–126 |
| Ib-9 | CH₃ | 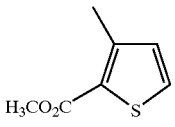 | 112–115 |
| Ib-10 | H | 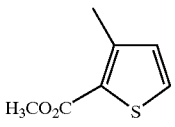 | 133–136 |
| Ib-11 | C₃H₇-iso | 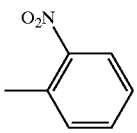 | 59–63 |
| Ib-12 | 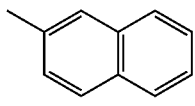 | | |

TABLE 2-continued
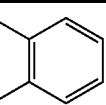
(Ib)
| Compound No. | R¹ | R² | mp (° C.) or $n_D^{20}$ |
|---|---|---|---|
| Ib-13 | 3-NO₂-C₆H₄ | 2-naphthyl | |
| Ib-14 | 4-NO₂-C₆H₄ | 2-naphthyl | |
| Ib-15 | CH₃ | 2-naphthyl | 127–128 |
| Ib-16 | H | 2-naphthyl | |
| Ib-17 | 4-Cl-C₆H₄ | 2-thienyl | |
| Ib-18 | 4-NO₂-C₆H₄ | 2-thienyl | |
| Ib-19 | C₆H₅ | 2-thienyl | 147–153 |
| Ib-20 | CH₃ | 2-thienyl | 96–98 |
| Ib-21 | H | 2-thienyl | 171–174 |
| Ib-22 | C₃H₇-iso | 2-thienyl | 53–55 |
| Ib-23 | 4-NO₂-C₆H₄ | 3,5-dimethyl-4-isoxazolyl | |
| Ib-24 | CH₃ | 3,5-dimethyl-4-isoxazolyl | 153–155 |

TABLE 2-continued
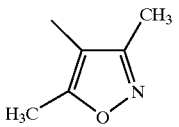
(Ib)
| Compound No. | R¹ | R² | mp (° C.) or $n_D^{20}$ |
|---|---|---|---|
| Ib-25 | H | 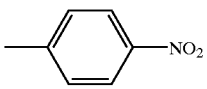 | 127–132 |
| Ib-26 | 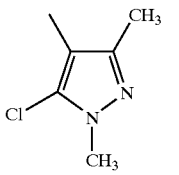 | 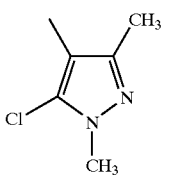 | |
| Ib-27 | H | 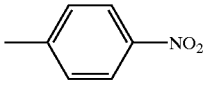 | |
| Ib-28 | 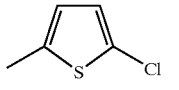 | 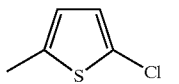 | 161–162 |
| Ib-29 | CH₃ | 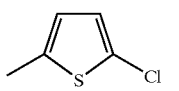 | 100–102 |
| Ib-30 | H | 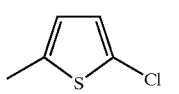 | 154–155 |
| Ib-31 | C₃H₇-iso | 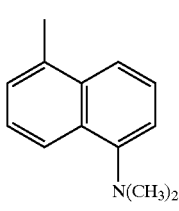 | 82–84 |
| Ib-32 | H | 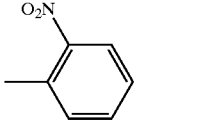 | |
| Ib-33 | H | C₂H₅ | |
| Ib-34 |  | C₈H₁₇-n | |

TABLE 2-continued (Ib)

| Compound No. | R¹ | R² | mp (° C.) or $n_D^{20}$ |
|---|---|---|---|
| Ib-35 | 3-NO₂-C₆H₄-CH₂- (3-nitrophenyl) | $C_8H_{17}$-n |  |
| Ib-36 | 4-Cl-C₆H₄- | $C_8H_{17}$-n | 1.5590 |
| Ib-37 | 4-NO₂-C₆H₄- | $C_8H_{17}$-n | 101–102 |
| Ib-38 | CH₃ | $C_8H_{17}$-n | 47–51 |
| Ib-39 | H | CF₃ | 138–144 |
| Ib-40 | H | —CH=CH—C₆H₅ |  |
| Ib-41 | 2-NO₂-C₆H₄- | —CH₂—C₆H₅ |  |
| Ib-42 | 3-NO₂-C₆H₄- | —CH₂—C₆H₅ |  |
| Ib-43 | 4-NO₂-C₆H₄- | —CH₂—C₆H₅ |  |
| Ib-44 | CH₃ | —CH₂—C₆H₅ | 127–129 |
| Ib-45 | H | —CH₂—C₆H₅ |  |
| Ib-46 | H | CH₂CF₃ |  |
| Ib-47 | 2,3-Cl₂-4-OH-C₆H₂- | CH₃ | 218–219 |

TABLE 2-continued
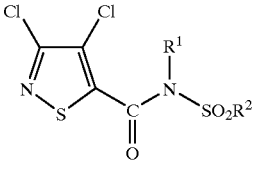
(Ib)
| Compound No. | R¹ | R² | mp (° C.) or $n_D^{20}$ |
|---|---|---|---|
| Ib-48 | 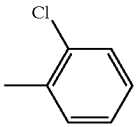 2-Cl-C₆H₄-CH₂- | CH₃ | 117–119 |
| Ib-49 | 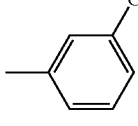 2-O₂N-C₆H₄-CH₂- | CH₃ | |
| Ib-50 | 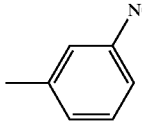 3-Cl-C₆H₄-CH₂- | CH₃ | 47–55 |
| Ib-51 | 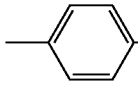 3-O₂N-C₆H₄-CH₂- | CH₃ | |
| Ib-52 | 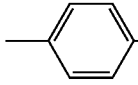 4-F-C₆H₄-CH₂- | CH₃ | |
| Ib-53 | 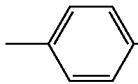 4-Br-C₆H₄-CH₂- | CH₃ | |
| Ib-54 | 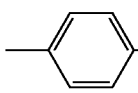 4-CH₃-C₆H₄-CH₂- | CH₃ | 122–124 |
| Ib-55 | 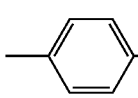 4-Cl-C₆H₄-CH₂- | CH₃ | 142–144 |
| Ib-56 | 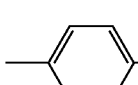 4-Cl-C₆H₄-CH₂- | CH₃ | |
| Ib-57 | 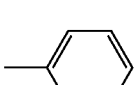 4-O₂N-C₆H₄-CH₂- | CH₃ | 147–149 |
| Ib-58 | C₆H₅-CH₂- | CH₃ | 151–153 |
| Ib-59 | CH₃ | CH₃ | 145–148 |

TABLE 2-continued

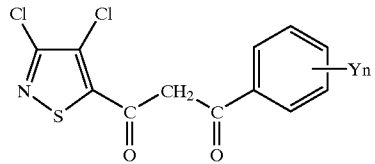

(Ib)

| Compound No. | R¹ | R² | mp (° C.) or $n_D^{20}$ |
|---|---|---|---|
| Ib-60 | cyclohexyl-H | $CH_3$ | 111–112 |
| Ib-61 | H | $CH_3$ | 153–155 |
| Ib-62 | $C_3H_7$-iso | $CH_3$ | |
| Ib-63 | $N(CH_3)_2$ | $CH_3$ | 200–201 |
| Ib-64 | —N(CH₃)(phenyl) | $CH_3$ | 213–215 |
| Ib-65 | H | $C_3H_7$-iso | |
| Ib-66 | H | $N(CH_3)_2$ | |
| Ib-67 | $C_3H_7$-iso | $N(CH_3)_2$ | 75–78 |
| Ib-68 | H | $C_{10}H_{21}$-n | |
| Ib-69 | H | $C_{12}H_{25}$-n | |
| Ib-70 | H | $C_{18}H_{37\text{-}1}$-n | |
| Ib-71 | H | $C_3H_7$-n | |
| Ib-72 | H | $C_4H_9$-n | |
| Ib-73 | H | $C_8H_{17}$-n | |

TABLE 3

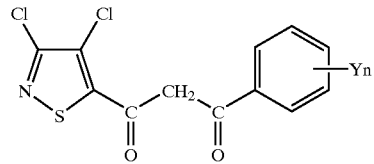

(Ic)

| Compound No. | $Y_n$ | mp (° C.) or $n_D^{20}$ |
|---|---|---|
| Ic-1 | 2,3,4-$(OCH_3)_3$ | |
| Ic-2 | 2,3,4,5,6-$(CH_3)_5$ | |
| Ic-3 | 2,3,4,5,6-$F_5$ | |
| Ic-4 | 2,3,4,5-$F_4$ | |
| Ic-5 | 2,3,4-$Cl_3$ | 183–184 |
| Ic-6 | 2,3,5,6-$(CH_3)_4$ | |
| Ic-7 | 2,3,6-$(CH_3)_3$ | |
| Ic-8 | 2,3,6-$F_3$ | |
| Ic-9 | 2,3-$Cl_2$ | 208 |
| Ic-10 | 2,3-$F_2$ | |
| Ic-11 | 2,4-$(CH_3)_2$ | |
| Ic-12 | 2,4-$(OCH_3)_2$ | |
| Ic-13 | 2,4,5-$(CH_3)_3$ | |
| Ic-14 | 2-$CH_3$, 4,5-$(OCH_3)_2$ | |
| Ic-15 | 2,4,5-$F_3$ | |
| Ic-16 | 2,4,6-$(CH_3)_3$ | 95 |
| Ic-17 | 2,4-$Cl_2$ | 140–143 |
| Ic-18 | 2,4-$Cl_2$, 5-F | |
| Ic-19 | 2,4-$F_2$ | |
| Ic-20 | 2,5-$(CH_2CF_3)_2$ | |
| Ic-21 | 2,5-$(CH_3)_2$ | 150–151 |
| Ic-22 | 2,5-$(OCH_3)_2$ | |
| Ic-23 | 2,5-$Cl_2$ | 203–205 |
| Ic-24 | 2,5-$F_2$ | |
| Ic-25 | 2,6-$(OCH_3)_2$ | |
| Ic-26 | 2,6-$CH_3$, 4-$C_4H_9$-tert | |
| Ic-27 | 2,6-$Cl_2$ | |
| Ic-28 | 2,6-$Cl_2$, 4-$CF_3$ | |
| Ic-29 | 2,6-$F_2$ | |
| Ic-30 | 2-Br | 128–130 |
| Ic-31 | 2-Br, 4,5-$O(CH_2)_2O$— | |
| Ic-32 | 2-phenyl | |
| Ic-33 | 2-$CF_3$ | 103–105 |
| Ic-34 | 2-$CF_3$, 4-F | |
| Ic-35 | 2-$CH_3$ | 150–151 |
| Ic-36 | 2-$CH_3$, 4,5-$(OCH_3)_2$ | 137–138 |
| Ic-37 | 2-Cl, 4-$CF_3$ | 84–85 |
| Ic-38 | 2-Cl | 150–151 |
| Ic-39 | 2-Cl, 4-O-(4-Cl-phenyl) | |

TABLE 3-continued

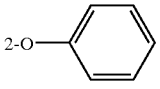

(Ic)

| Compound No. | Y$_n$ | mp (° C.) or n$_D^{20}$ |
|---|---|---|
| Ic-40 | 2-Cl, 5-CF$_3$ | |
| Ic-41 | 2-F | |
| Ic-42 | 2-F, 3-CF$_3$ | |
| Ic-43 | 2-F, 4-CF$_3$ | |
| Ic-44 | 2-F, 4-OCH$_3$ | |
| Ic-45 | 2-F, 5-CF$_3$ | |
| Ic-46 | 2-F, 6-CF$_3$ | |
| Ic-47 | 2-NO$_2$ | 148–152 |
| Ic-48 | 2-NO$_2$, 4,5-OCH$_2$O— | |
| Ic-49 | 2-OC$_6$H$_{13}$-n | |
| Ic-50 | 2-O—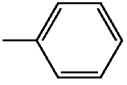 | |
| Ic-51 | 2-OCH$_3$ | |
| Ic-52 | 2-OCH$_3$, 3-CH$_3$, 4-O—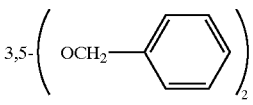 | |
| Ic-53 | 2-OCH$_3$, 4-F | |
| Ic-54 | 2-OCH$_3$, 4-Cl | 163–164 |
| Ic-55 | 2-OCH$_3$, 5-Cl | |
| Ic-56 | 3,4-(CH$_2$)$_3$— | |
| Ic-57 | 3,4-(CH$_3$)$_2$ | 160–161 |
| Ic-58 | 3,4-(OCH$_3$)$_2$ | 140–143 |
| Ic-59 | 3,4,5-(OCH$_3$)$_3$ | |
| Ic-60 | 3,4-C(CH$_3$)$_2$CH$_2$CH$_2$C(CH$_3$)$_2$— | |
| Ic-61 | 3,4-Cl$_2$ | 128–130 |
| Ic-62 | 3,4-F$_2$ | 113–114 |
| Ic-63 | 3,4-O(CH$_2$)$_3$O— | |
| Ic-64 | 3,4-OCH$_2$CH$_2$O— | |
| Ic-65 | 3,4-OCH$_2$O— | |
| Ic-66 | 3,5-(CF$_3$)$_2$ | 151–155 |
| Ic-67 | 3,5-(CH$_3$)$_2$ | |
| Ic-68 | 3,5-(OCH$_2$—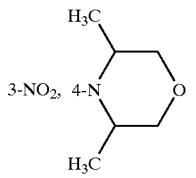)$_2$ | |
| Ic-69 | 3,5-(OCH$_3$)$_2$ | |
| Ic-70 | 3,5-Cl$_2$ | 179–180 |
| Ic-71 | 3,5-F$_2$ | |
| Ic-72 | 3-Br | |
| Ic-73 | 3-Br, 4-F | 124–132 |
| Ic-74 | 3-C$_2$H$_5$ | |
| Ic-75 | 3-CF$_3$ | |
| Ic-76 | 3-CF$_3$, 4-F | |
| Ic-77 | 3-CH$_3$ | 107–108 |
| Ic-78 | 3-CH$_3$, 4-Cl | |
| Ic-79 | 3-Cl | 135 |
| Ic-80 | 3-Cl, 4-F | |
| Ic-81 | 3-Cl, 4-OCH$_3$ | 171–172 |
| Ic-82 | 3-Cl, 4-OCH$_2$OC$_2$H$_5$ | |
| Ic-83 | 3-Cl, 4-OH | |
| Ic-84 | 3-CN | |
| Ic-85 | 3-CO$_2$C$_2$H$_5$, 4-OC$_2$H$_5$ | |
| Ic-86 | 3-F | |
| Ic-87 | 3-F, 4-OCH$_3$ | |
| Ic-88 | 3-F, 5-CF$_3$ | |
| Ic-89 | 3-NO$_2$ | 197–199 |
| Ic-90 | 3-NO$_2$, 4-N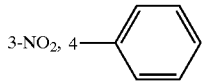 | |
| Ic-91 | 3-NO$_2$, 4-Br | |
| Ic-92 | 3-NO$_2$, 4—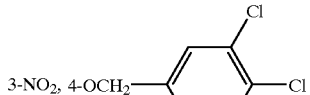 | |
| Ic-93 | 3-NO$_2$, 4-Cl | |
| Ic-94 | 3-NO$_2$, 4-OCH$_2$—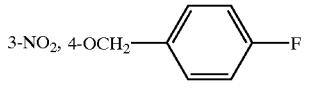 | |
| Ic-95 | 3-NO$_2$, 4-OCH$_2$—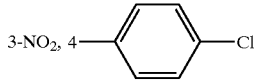 | |
| Ic-96 | 3-NO$_2$, 4-OCH$_3$ | |
| Ic-97 | 3-NO$_2$, 4—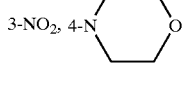 | |
| Ic-98 | 3-NO$_2$, 4-N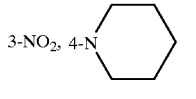 | |
| Ic-99 | 3-NO$_2$, 4-N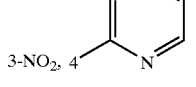 | |
| Ic-100 | 3-NO$_2$, 4—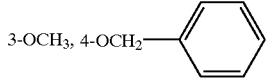 | |
| Ic-101 | 3-NO$_2$, 4-CH$_3$ | |
| Ic-102 | 3-OCF$_3$ | |
| Ic-103 | 3-OCH$_3$ | 111–112 |
| Ic-104 | 3-OCH$_3$, 4-OCH$_2$— | |
| Ic-105 | 3-OC$_3$H$_7$-iso | 77–79 |

TABLE 3-continued

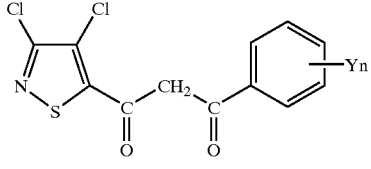
(Ic)

| Compound No. | $Y_n$ | mp (° C.) or $n_D^{20}$ |
|---|---|---|
| Ic-106 | 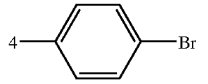 4- (4,5-dichloroimidazol-1-yl) | |
| Ic-107 | 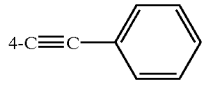 4-(4-bromophenyl) | |
| Ic-108 | 4-Br | 167–168 |
| Ic-109 |  4-C≡C-phenyl | |
| Ic-110 | 4-C$_2$H$_5$ | |
| Ic-111 |  4-phenyl | 162 |
| Ic-112 | 4-CF$_3$ | 128–130 |
| Ic-113 | 4-CH$_3$ | 140–142 |
| Ic-114 | 4-Cl | 149–151 |
| Ic-115 | 4-CN | 199 |
| Ic-116 | 4-CO$_2$CH$_3$ | |
| Ic-117 | 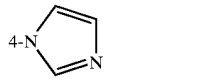 4-cyclohexyl | |
| Ic-118 | 4-F | |
| Ic-119 | 4-I | |
| Ic-120 | 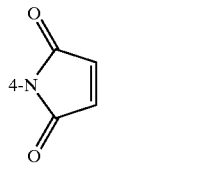 4-(imidazol-1-yl) | |
| Ic-121 | 4-C$_3$H$_7$-iso | |
| Ic-122 | 4-C$_4$H$_9$-iso | 90–92 |
| Ic-123 | 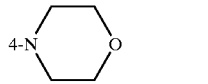 4-(maleimido) | |
| Ic-124 | 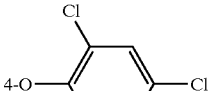 4-(morpholino) | |
| Ic-125 | 4-N(CH$_3$)$_2$ | 223–224 |
| Ic-126 | 4-N(C$_2$H$_5$)$_2$ | |
| Ic-127 | 4-C$_{10}$H$_{21}$-n | |
| Ic-128 | 4-C$_3$H$_7$-n | |

TABLE 3-continued

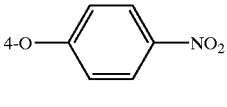
(Ic)

| Compound No. | $Y_n$ | mp (° C.) or $n_D^{20}$ |
|---|---|---|
| Ic-129 | 4-C$_4$H$_9$-n | |
| Ic-130 | 4-C$_5$H$_{11}$-n | |
| Ic-131 | 4-C$_6$H$_{13}$-n | |
| Ic-132 | 4-C$_7$H$_{15}$-n | |
| Ic-133 | 4-C$_8$H$_{17}$-n | |
| Ic-134 | 4-C$_9$H$_{19}$-n | |
| Ic-135 | 4-NO$_2$ | 178–179 |
| Ic-136 | 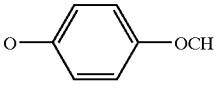 4-O-(2,4-dichlorophenyl) | |
| Ic-137 | 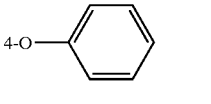 4-O-(4-nitrophenyl) | |
| Ic-138 | 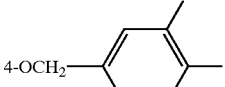 4-O-(4-methoxyphenyl) | |
| Ic-139 | 4-OC$_2$H$_5$ | |
| Ic-140 | 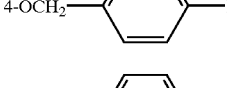 4-O-phenyl | 130–131 |
| Ic-141 | 4-OCF$_3$ | 150–151 |
| Ic-142 | 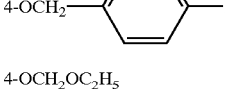 4-OCH$_2$-(3,4-dichlorophenyl) | |
| Ic-143 | 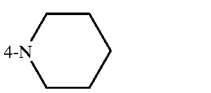 4-OCH$_2$-(4-fluorophenyl) | |
| Ic-144 | 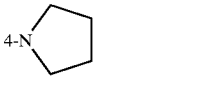 4-OCH$_2$-(4-nitrophenyl) | |
| Ic-145 | 4-OCH$_2$OC$_2$H$_5$ | 174 |
| Ic-146 | 4-OCH$_3$ | 138–139 |
| Ic-147 | 4-OCHF$_2$ | |
| Ic-148 | 4-OH | 224–227 |
| Ic-149 | 4-OC$_4$H$_9$-n | |
| Ic-150 | 4-(piperidin-1-yl) | |
| Ic-151 | 4-(pyrrolidin-1-yl) | |

TABLE 3-continued (Ic)

[Structure: 3,4-dichloroisothiazol-5-yl-C(O)-CH₂-C(O)-phenyl-Yn]

| Compound No. | Yₙ | mp (° C.) or $n_D^{20}$ |
|---|---|---|
| Ic-152 | 4-S-phenyl | |
| Ic-153 | 4-SCH₃ | |
| Ic-154 | 4-C₄H₉-sec | |
| Ic-155 | 4-SO₂-phenyl | |
| Ic-156 | 4-C₄H₉-tert | 150–151 |
| Ic-157 | | 109–112 |

TABLE 4

(Id)

[Structure: 3,4-dichloroisothiazol-5-yl-C(O)-CH₂-C(O)-R⁵]

| Compound No. | R⁵ | mp (° C.) or $n_D^{20}$ |
|---|---|---|
| Id-1 | 1,1,4-trimethyl-6-tert-butyl-indan-yl | |
| Id-2 | 4-fluoro-1-naphthyl | |
| Id-3 | 1-naphthyl | |
| Id-4 | 5-(2,3-dihydrobenzofuran)yl | |
| Id-5 | 1,6-dimethylnaphthyl | |
| Id-6 | 6-methoxy-2-methylnaphthyl | |
| Id-7 | 2-naphthyl | |
| Id-8 | 2,3-dimethylpyrazinyl | |
| Id-9 | 2-methylpyrazinyl | |
| Id-10 | 3-pyridyl | |
| Id-11 | 2-pyridyl | 140–143 |
| Id-12 | 1-methyl-3-methylpyrrolyl | 174–175 |
| Id-13 | 1,2-dimethylpyrrolyl | 177 |
| Id-14 | 5-chloro-2-methylthienyl | 113–114 |
| Id-15 | 3-methylbenzothiophen-yl | |

TABLE 4-continued
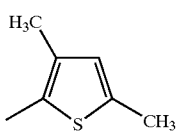
(Id)
| Compound No. | R⁵ | mp (° C.) or $n_D^{20}$ |
|---|---|---|
| Id-16 | 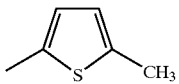 | |
| Id-17 | 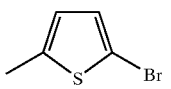 | |
| Id-18 | 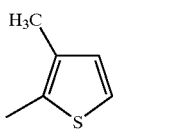 | |
| Id-19 | 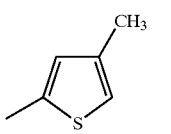 | |
| Id-20 | 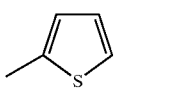 | |
| Id-21 | 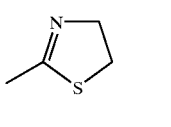 | |
| Id-22 | 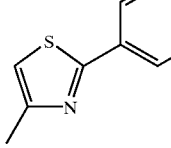 | |
| Id-23 | 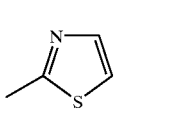 | 155–160 |
| Id-24 | 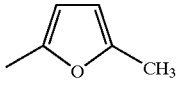 | 146–148 |
| Id-25 | 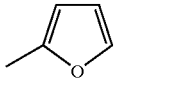 | 122–124 |
| Id-26 | 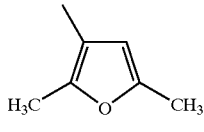 | 139–144 |
| Id-27 | 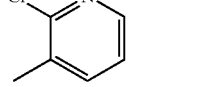 | 114–116 |
| Id-28 | 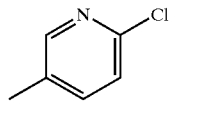 | |
| Id-29 | 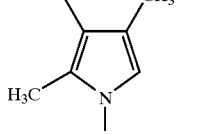 | 115–116 |
| Id-30 | 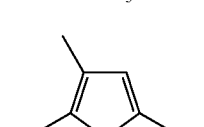 | |
| Id-31 | 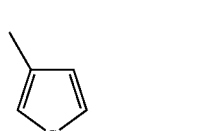 | 132–134 |
| Id-32 | 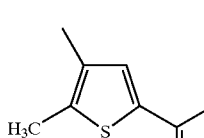 | |
| Id-33 | 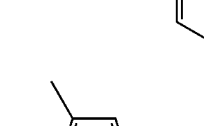 | |
| Id-34 | | |
| Id-35 | 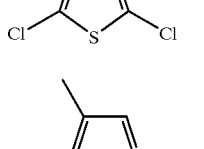 | |

TABLE 4-continued (Id)

[Structure: 3,4-dichloroisothiazol-5-yl-C(=O)-CH₂-C(=O)-R⁵]

| Compound No. | R⁵ | mp (° C.) or $n_D^{20}$ |
|---|---|---|
| Id-36 | 1,4-dimethyl-3-pyrazolyl (1-CH₃, 4-CH₃) | 125–126 |
| Id-37 | 2,4-dimethylthiazol-5-yl | |
| Id-38 | 5,6,7,8-tetrahydronaphthalen-2-yl | |
| Id-39 | 5-methyl-4-phenyl-1,2,3-thiadiazol-yl | |
| Id-40 | 2,4-dimethylthiazol-5-yl (with CH₃ at 4, H₃C at another position) | 129–130 |
| Id-41 | 2,5-dimethylthiazol-4-yl | |
| Id-42 | 2,5-dimethyl-2,3-dihydrobenzofuran-yl | |
| Id-43 | 7-methylbenzo[1,2,3]thiadiazol-yl | |

TABLE 5

(Ie)

[Structure: 3,4-dichloroisothiazol-5-yl-C(=O)-CH(R³)-C(=O)-R⁴]

| Compound No. | $-\underset{|}{C}H-\underset{\overset{\|}{O}}{C}-R^4$ with R³ | mp (° C.) or $n_D^{20}$ |
|---|---|---|
| Ie-1 | R³=CN, R⁴=OCH₃ (—CHCN—CO₂CH₃) | 119–122 |
| Ie-2 | R³=SO₂Ph, R⁴=OC₂H₅ (—CHSO₂Ph—CO₂C₂H₅) | 100–103 |
| Ie-3 | R³=CN, R⁴=OC₃H₇-iso (—CHCN—CO₂C₃H₇-iso) | 105–106 |
| Ie-4 | R³=CO₂C₂H₅, R⁴=phenyl | 1.5922 |
| Ie-5 | R³=CN, R⁴=phenyl | 154–156 |
| Ie-6 | 2-methyl-5-(4-chlorophenyl)-cyclohexane-1,3-dione derivative | 127–129 |
| Ie-7 | R³=CN, R⁴=3,5-dimethylphenyl | 115–122 |
| Ie-8 | R³=CN, R⁴=3-methoxyphenyl | 147–148 |

TABLE 5-continued

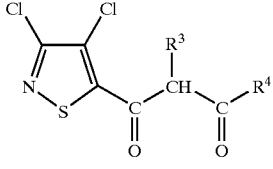

(Ie)

| Compound No. | 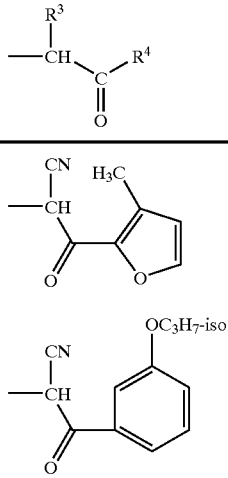 | mp (° C.) or $n_D^{20}$ |
|---|---|---|
| Ie-9 | (structure: CH(CN) attached to C(=O)-furan with H3C substituent) | 179–181 |
| Ie-10 | (structure: CH(CN)-C(=O)-phenyl with OC3H7-iso substituent) | 96–98 |

BIOLOGICAL TEST EXAMPLES

Test Example A

Test of foliar spray effect against *Pyricularia oryzae*

Preparation of Formulations of the Compounds Tested

Active compound: 30–40 parts by weight

Carrier: mixture of diatomaceous earth and kaolin (1:5), 55–65 parts by weight

Emulsifier: polyoxyethylene alkyl phenyl ether, 5 parts by weight

The above-mentioned amounts of active compound, carrier and emulsifier are crushed and mixed to make a wettable powder. A portion of the wettable powder comprising the prescribed amount of active compound is diluted with water and used for testing.

Testing Procedure

Seedlings of paddy rice (cultivar: Kusabue) were cultured in plastic pots each having a diameter of 6 cm. The previously prepared solution of the prescribed concentration of active compound was sprayed over the seedlings in the 1.5–2 leaf stage, at a rate of 20 ml per 3 pots. 5 days after the application, a suspension of spores of artificially cultured *Pyricularia oryzae* sprayed on the test plants once for inoculation, and the plants were kept at 25° C. and 100% relative humidity for infection. 7 days after the inoculation, the infection rate per pot was classified and evaluated according to the following standard and the control value (%) was calculated. Phytotoxicity was tested at the same time. This test is an average of the results of 3 replications. The evaluation of the infection rate and the calculation method of the control value are identical in each of the Test Examples A–C.

| Infection rate | Percentage of lesion area in (%) |
|---|---|
| 0 | 0 |
| 0.5 | less than 2 |
| 1 | 2–less than 5 |
| 2 | 5–less than 10 |
| 3 | 10–less than 20 |
| 4 | 20–less than 40 |
| 5 | more than 40 |

$$\text{Control value (\%)} = \left(1 - \frac{\text{Infection rate of treated section}}{\text{Infection rate of untreated section}}\right) \times 100$$

Test Results

Compounds No. Ia-1, Ia-10, Ia-37, Ia-46, Ia-56, Ia-91, Ia-92, Ia-93, Ia-96, Ia-98, Ia-100, Ia-103, Ia-112, Ia-117, Ia-118, Ib-6, Ib-10, Ib-19, Ib-20, Ib-22, Ib-24, Ib-30, Ib-37, Ib-38, Ib-47, Ib-55, Ib-57, Ic-5, Ic-16, Ic-23, Ic-30, Ic-33, Ic-37, Ic-38, Ic-47, Ic-57, Ic-62, Ic-66, Ic-73, Ic-77, Ic-89, Ic-103, Ic-105, Ic-108, Ic-112, Ic-113, Ic-125, Ic-135, Ic-148, Ic-157, Id-11, Id-12, Id-13, Id-23, Id-25, Id-26, Id-27, Id-31, Id-36, Id-40, Ie-1, Ie-2, Ie-3, Ie-4, Ie-5 and Ie-6 showed control values of more than 80% at an active compound concentration of 500 ppm. No phytotoxicity was observed.

Test Example B

Test of water surface application effect against *Pyricularia oryzae*.

Testing Procedure

Seedlings of paddy rice (cultivar: Kusabue) in the 1.5 leaf stage were cultivated in plastic pots each having a diameter of 6 cm. The seedlings were then transplanted into irrigated plastic cups each having a diameter of 10 cm, one seedling per pot, and the water just covering the soil. The solution of the prescribed concentration of the active compound, which had been prepared in the same manner as that of Test Example A, was dropped to the water surface with a pipette at a rate of 5 ml per pot. 7 days after the chemical treatment, a suspension of spores of artificially cultured *Pyricularia oryzae* was sprayed once on the test plants for inoculation, and the plants were kept at a temperature of 25° C. and a relative atmospheric humidity of 100%. Seven days after the inoculation, the infection rate per pot was classified and evaluated, and further the control value (%) was calculated. Phytotoxicity was tested at the same time.

This test is an average of the results of 3 replications.

Test Results

Compounds No. Ia-1, Ia46, Ia-58, Ia-68, Ia-76, Ia-83, Ia-84, Ia-86, Ia-99, Ia-103, Ia-125, Ia-132, Ib-1, Ib-3, Ib-15, Ib-36, Ib-39, Ib-54, Ib-55, Ib-58, Ib-60, Ic-63, Ic-5, Ic-9, Ic-36, Ic-37, Ic-38, Ic-57, Ic-58, Ic-66, Ic-70, Ic-105, Ic-122, Ic-125, Ic-145, Ic-148, Id-12, Id-13, Id-14, Id-23, Id-27, Id-31, Id-40, Ie-1, Ie-4, Ie-5 and Ie-6 showed control values of more than 80% at an active compound dosage of 8 kg/ha No phytotoxicity was observed.

Test Example C

Test for the effect of seed treatment against *Pyricularia oryzae*

Testing Procedure

Seeds of paddy rice (cultivar: Kasabue) were soaked in a diluted solution of an active compound having the prescribed concentration. 5 ml of such solution, which had been prepared in the same manner as that of Test Example A, were used per 150 grains of seed. Soaking was conducted at a temperature of 20° C. for 5 days. After the soaking, the air-dried seeds were sown in 2 plastic pots, each having a diameter of 9 cm, and the seeds were germinated by placing the pots in a warmed nursery box (32° C.) for 3 days. After cultivating the seedlings for 2 weeks, the plants reached the 2–2.5 leaf stage. A spore suspension of artificially cultured *Pyricularia oryzae* was then sprayed on the test plants once, and the plants were kept at a temperature of 25° C. and a relative atmospheric humidity of 100% for infection. Seven days after the inoculation, the infection rate per pot was classified and evaluated and the control value (%) was calculated. Phytotoxicity was tested at the same time.

This test is an average of the results of 2 replications.

Test Results

Compounds No. Ia-10, Ia-46, Ia-62, Ia-68, Ia-76, Ia-77, Ia-83, Ia-88, Ia-93, Ia-96, Ia-98, Ia-99, Ia-100, Ia-101, Ia-102, Ia-103, Ia-109, Ia-112, Ia-117, Ib-1, Ib-3, Ib-15, Ib-21, Ib-37, Ib-38, Ib-39, Ib-48, Ib-50, Ib-55, Ib-57, Ib-61, Ic-5, Ic-9, Ic-17, Ic-30, Ic-33, Ic-35, Ic-36, Ic-38, Ic-54, Ic-57, Ic-62, Ic-70, Ic-73, Ic-77, Ic-79, Ic-103, Ic-105, Ic-111, Ic-112, Ic-113, Ic-114, Ic-115, Ic-122, Ic-148, Ic-157, Id-11, Id-12, Id-14, Id-24, Id-25, Id-26, Id-27, Id-29, Id-36, Ie-3, Ie-4 and Ie-5 showed control values of more than 80% at an active compound concentration of 500 ppm. No phytotoxicity was observed.

FORMULATION EXAMPLES

Formulation Example I (Granules)

25 parts by weight of water were added to a mixture of 10 parts by weight of Compound No. Ic-5 according to the invention, 30 parts by weight of bentonite (montmorillonite), 58 parts by weight of talc and 2 parts by weight of lignin sulphonic acid salt, and the mixture was kneaded thoroughly. The resulting product was granulated by means of an extrusion granulator to form granules having a size of from 10 to 40 meshes. The granules were dried at a temperature between 40 and 50° C.

Formulation Example II (Granules)

95 parts by weight of a clay mineral having a particle size distribution within a range of from 0.2 to 2 mm were introduced into a rotary mixer. This product was uniformly wetted by spraying thereto under rotation a mixture of 5 parts by weight of Compound No. Id-12 according to the invention and a liquid diluent. The granules obtained in this manner were dried at a temperature between 40 and 50° C.

Formulation Example III (Emulsifiable Concentrate)

An emulsifiable concentrate was prepared by mixing 30 parts by weight of Compound No. Ie-4 according to the invention, 5 parts by weight of xylene, 8 parts by weight of polyoxyethylene alkyl phenyl ether and 7 parts by weight of calcium alkylbenzene sulphonate with stirring.

Formulation Example IV (Wettable Powder)

A wettable powder was prepared by thoroughly mixing 15 parts by weight of Compound No. Ia-46 according to the invention, 80 parts by weight of a mixture (1:5) of White Carbon (fine powder of hydrated non-crystalline silicon oxide) and powdery clay, 2 parts by weight of sodium alkylbenzene sulphonate and 3 parts by weight of a condensate of sodium alkylnaphthalene sulphonate and formaldehyde in powdery state.

Formulation Example V (Wettable Granules)

20 parts by weight of Compound No. Ib-55 according to the invention, 30 parts by weight of sodium lignin sulphonate, 15 parts by weight of bentonite and 35 parts by weight of calcined diatomaceous earth powder were thoroughly mixed with water. The resulting product was granulated by means of extrusion through a 0.3 mm screen. After drying the product, wettable granules were obtained.

What is claimed is:

1. An isothiazole derivative of the formula (I)

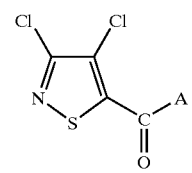

(I)

wherein A represents a substituent selected from the group consisting of

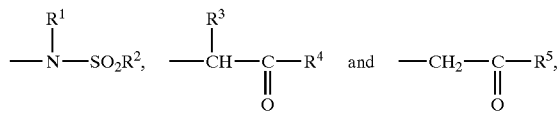

in which $R^1$ represents hydrogen; $C_{1-6}$ alkyl; $C_{3-6}$ cycloalkyl; $C_{3-6}$ alkenyl; $C_{3-6}$ alkinyl; $C_{3-6}$ epoxyalkyl; 1-($C_{3-4}$ alkoxycarbonyl)-$C_{1-6}$ alkyl; phenyl that is optionally substituted by 1 to 3 radicals selected from the group consisting of halogen, $C_{1-6}$ alkyl, nitro, cyano, and hydroxyl; $C_{1-6}$ alkoxycarbonyl; di-($C_{1-6}$ alkyl)-amino; or N—$C_{1-6}$ alkylanilino;

$R^2$ represents $C_{1-18}$ alkyl; $C_{1-6}$ haloalkyl; phenyl that is optionally substituted by 1 to 5 radicals selected from the group consisting of halogen, $C_{1-6}$ alkyl, $C_{1-6}$ haloalkyl, $C_{1-6}$ alkoxy, $C_{1-6}$ haloalkoxy, phenol, cyano, amino, hydroxy, nitro, and phenoxy that is in turn optionally substituted by 1 to 3 radicals selected from halogen and cyano; naphthyl that is optionally substituted by di-($C_{1-4}$ alkyl)-amino; a 5-membered heterocyclic group having 1 or 2 hetero atoms selected from the group consisting of nitrogen, oxygen, and sulfur wherein the heterocyclic ring isoptionally substituted by 1 to 3 identical or different radicals selected from the group consisting of halogen, $C_{1-6}$ alkyl, and $C_{1-4}$ alkoxycarbonyl; $C_{7-9}$ aralkyl; $C_{2-4}$ alkenyl; phenyl-$C_{2-4}$ alkenyl; di-($C_{1-6}$ alkyl)-amino; or camphor-10-yl;

$R^3$ represents $C_{1-4}$ alkoxycarbonyl, cyano, or phenylsulfonyl;

R⁴ represents phenyl that is optionally substituted by 1 to 3 identical or different radicals selected from the group consisting of $C_{1-4}$ alkyl and $C_{1-4}$ alkoxy; furyl that is optionally substituted by 1 to 3 identical or different $C_{1-4}$ alkyl radicals; or $C_{1-6}$ alkoxy; or $R^3$ and $R^4$, together with the carbon atoms to which they are bonded, form a phenyl-substituted cyclohexanedione ring wherein the phenyl ring is optionally substituted by halogen; and $R^5$ represents (i) phenyl that is optionally substituted by 1 to 5 identical or different radicals selected from the group consisting of halogen, $C_{1-10}$ alkyl, $C_{3-6}$ cycloalkyl, $C_{1-6}$ haloalkyl, $C_{2-4}$ alkinyl, phenyl-$C_{2-4}$ alkinyl, $C_{1-6}$ alkoxy, $C_{1-6}$ haloalkoxy, $C_{1-4}$ alkoxymethoxy, benzyloxy that is in turn optionally substituted by halogen and/or nitro, phenyl that is in turn optionally substituted by halogen, phenoxy that is in turn optionally substituted by halogen, $C_{1-4}$ alkoxy, and/or nitro, $C_{1-4}$ alkoxycarbonyl, 5- or 6-membered heterocyclyl having 1 or 2 nitrogen atoms or 1 nitrogen atom and 1 oxygen atom wherein the heterocyclic ring is optionally substituted by 1 to 3 identical or different radicals selected from the group consisting of halogen, $C_{1-4}$ alkyl, and oxo, di-($C_{1-4}$ alkyl)amino, $C_{1-4}$ alkylthio, phenylthio, phenylsulfonyl, hydroxy, nitro, and cyano, or phenyl in which two adjacent substituents form a $C_{1-4}$ alkylenedioxy group or a $C_{3-8}$ alkylene group; (ii) naphthyl that is optionally substituted by 1 to 3 identical or different radicals selected from the group consisting of halogen, $C_{1-4}$ alkyl, and $C_{1-4}$ alkoxy; or (iii) a 5- or 6-membered heterocyclic group having 1 to 3 hetero atoms selected from the group consisting of nitrogen, oxygen, and sulfur wherein the heterocyclic ring is optionally substituted by 1 to 3 radicals selected from the group consisting of halogen, $C_{1-6}$ alkyl, phenyl, and nitro and is optionally condensed with a benzene ring.

2. An isothiazole derivative of the formula (I) according to claim 1 in which A represents a group selected from the group consisting of

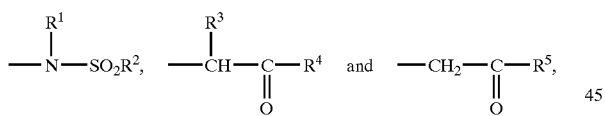

wherein $R^1$ represents hydrogen; $C_{1-6}$ alkyl; $C_{5-6}$ cycloalkyl; $C_{3-4}$ alkenyl; $C_{3-4}$ alkinyl; $C_{3-4}$ epoxyalkyl; 1-($C_{1-2}$ alkoxycarbonyl)-$C_{1-4}$ alkyl; phenyl that is optionally substituted by 1 to 3 identical or different radicals selected from the group consisting of fluoro, chloro, bromo, $C_{1-4}$ alkyl, nitro, cyano, and hydroxy; $C_{1-4}$ alkoxycarbonyl; di-($C_{1-4}$ alkyl)amino; or N—$C_{1-4}$ alkylanilino;

$R^2$ represents $C_{1-18}$ alkyl; $C_{1-4}$ haloalkyl; phenyl that is optionally substituted by 1 to 5 radicals selected from the group consisting of fluoro, chloro, bromo, $C_{1-5}$ alkyl, $C_{1-4}$ haloalkyl, $C_{1-4}$ alkoxy, $C_{1-4}$ haloalkoxy, phenyl, cyano, amino, hydroxy, nitro, and phenoxy that is in turn optionally substituted by 1 to 3 identical or different substituents selected from the group consisting of fluoro, chloro, bromo, and cyano; naphthyl that is optionally substituted by 1 or 2 di-($C_{1-2}$ alkylyamino groups; a 5-membered heterocyclic group having 1 or 2 heteroatoms selected from the group consisting of nitrogen, oxygen, and sulfur wherein the heterocylic ring is optionally substituted by 1 to 3 identical or different radicals selected from the group consisting of fluoro, chloro, $C_{1-4}$ alkyl, and $C_{1-2}$ alkoxycarbonyl; phenyl-$C_{1-2}$ alkyl; $C_{2-3}$ alkenyl; phenyl-$C_{2-3}$ alkenyl; di-($C_{1-4}$ alkylyamino; or camphor-10-yl;

$R^3$ represents $C_{1-2}$ alkoxycarbonyl, cyano, or phenylsulfonyl;

$R^4$ represents phenyl that is optionally substituted by 1 to 3 identical or different $C_{1-2}$ alkyl groups or $C_{1-4}$ alkoxy groups; furyl that is optionally substituted by 1 to 3 identical or different $C_{1-2}$ alkyl groups; or $C_{1-4}$ alkoxy; or $R^3$ and $R^4$, together with the carbon atoms to which they are bonded, form a phenyl-substituted cyclohexanedione ring wherein the phenyl ring is optionally mono- or di-substituted by fluoro and/or chloro; and $R^5$ represents (i) phenyl that is optionally substituted by 1 to 5 identical or different radicals selected from the group consisting of fluoro, chloro, bromo, iodo, $C_{1-9}$ alkyl, $C_{5-6}$ cycloalkyl, $C_{1-4}$ haloalkyl, phenylethinyl, $C_{1-6}$ alkoxy, $C_{1-4}$ haloalkoxy, $C_{1-3}$ alkoxymethoxy, benzyloxy that is in turn optionally substituted by 1 to 3 identical or different radicals selected from the group consisting of fluoro, chloro, and nitro, phenyl that is in turn optionally substituted by 1 to 3 radicals selected from the group consisting of chloro and bromo, phenoxy that is in turn optionally substituted by 1 to 3 identical or different radicals selected from the group consisting of chloro, $C_{1-2}$ alkoxy, and nitro, $C_{1-2}$ alkoxycarbonyl, 5- or 6-membered heterocyclyl having 1 or 2 nitrogen atoms or 1 nitrogen atom and 1 oxygen atom wherein the heterocyclic ring is optionally substituted by 1 to 3 identical or different radicals selected from the group consisting of chloro, $C_{1-2}$ alkyl, and oxo, di-($C_{1-2}$ alkyl)-amino, $C_{1-2}$ alkylthio, phenylthio, phenylsulfonyl, hydroxy, nitro, and cyano, or phenyl in which two adjacent substituents form a $C_{1-3}$ alkylenedioxy group or a $C_{3-8}$ alkylene group; (ii) naphthyl that is optionally substituted by 1 to 3 identical or different radicals selected from the group consisting of fluoro, chloro, methyl, ethyl, and methoxy; or (iii) a 5- or 6-membered heterocyclic group having 1 to 3 hetero atoms selected from the group consisting of nitrogen, oxygen, and sulfur wherein the heterocyclic ring is optionally substituted by 1 to 3 radicals selected from the group consisting of fluoro, chloro, bromo, $C_{1-4}$ alkyl, phenyl, and nitro and is optionally condensed with a benzene ring.

3. An isothiazole derivative of the formula (I) according to claim 1 in which A represents a group selected from the group consisting of

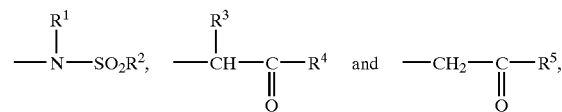

wherein $R^1$ represents hydrogen; methyl; ethyl; isopropyl; n-butyl; 1,3-dimethylbutyl; cyclohexyl; allyl; propargyl; 2,3-epoxypropyl; 2-methyl-1-methoxycarbonylpropyl; phenyl that is optionally substituted by 1 to 3 identical or different radicals selected from the group consisting of fluoro, chloro, bromo, methyl, nitro, cyano, and hydroxy; tert-butoxycarbonyl; dimethylamino; or N-methylanilino;

$R^2$ represents $C_{1-18}$ alkyl; 3-chloropropyl; trifluoromethyl; 2,2,2-trifluoroethyl; phenyl that is optionally substituted by 1 to 5 identical of different radicals selected from the group consisting of fluoro, chloro, bromo, $C_{1-5}$ alkyl; trifluoromethoxy, trifluoromethyl, methoxy, phenyl, cyano, amino, hydroxy, nitro, and phenoxy that is in turn optionally substituted by 1 to 3 identical or different substituents selected from the group consisting of fluoro, chloro, bromo, and cyano; naphthyl that is optionally substituted by dimethylamino; thienyl, isoxazolyl, or pyrazolyl, each of which thienyl, isoxazolyl, or pyrazolyl radicals is optionally substituted by 1 to 3 substituents selected from the group consisting of fluoro, chloro, methyl, and methoxycarbonyl; benzyl; allyl; dimethylamino; or camphor-10-yl;

$R^3$ represents methoxycarbonyl, ethoxycarbonyl, cyano, or phenylsulfonyl;

$R^4$ represents phenyl that is optionally substituted by 1 to 3 identical or different radicals selected from the group consisting of methyl, methoxy, and isopropoxy; furyl that is optionally substituted by 1 to 3 identical or different radicals selected from the group consisting of methyl and ethyl; methoxy; or isopropoxy; or $R^3$ and $R^4$, together with the carbon atoms to which they are bonded, form a phenyl-substituted cyclohexanedione ring wherein the phenyl ring is optionally substituted by chloro; and $R^5$ represents (I) phenyl that is optionally substituted by 1 to 5 identical or different radicals selected from the group consisting of fluoro, chloro, bromo, iodo, $C_{1-9}$ alkyl, cyclohexyl, trifluoromethyl, phenylethinyl, $C_{1-6}$ alkoxy, trifluoromethoxy, difluoromethoxy, ethoxymethoxy, benzyloxy that is in turn optionally substituted by 1 to 3 identical or different radicals selected from the group consisting of fluoro, chloro, and nitro, phenyl that is in turn optionally substituted by 1 to 3 radicals selected from the group consisting of chloro and bromo, phenoxy that is in turn optionally substituted by 1 to 3 identical or different radicals selected from the group consisting of chloro, methoxy, and nitro, methoxycarbonyl, ethoxycarbonyl, morpholinyl, pyrrolidinyl, piperidinyl, pyridinyl, or imidazolyl each or which morpholinyl, pyrrolidinyl, piperidinyl, pyridinyl, or imidazolyl heterocycles is optionally mono- or di-substituted by methyl and/or chloro, the radical of the formula

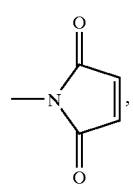

dimethylamino, methylthio, phenylthio, phenylsulfonyl, hydroxy, nitro, and cyano, or phenyl in which two adjacent substituents optionally form a $C_{1-3}$ alkylenedioxy group or a $C_{3-8}$ alkylene group; (ii) naphthyl that is optionally substituted by 1 to 3 identical radicals selected from the group consisting of fluoro, chloro, methyl, and methoxy; or (iii) a heterocyclic group selected from the group consisting of pyrrolyl, furanyl, dihydrofuranyl, thienyl, thiazolyl, 1,2,3-thiadiazolyl, pyridyl, pyrimidinyl, and pyrazolyl, wherein each heterocyclic radical is optionally substituted by 1 to 3 substituents selected from the group consisting of fluoro, chloro, methyl, phenyl, and nitro and is optionally condensed with a benzene ring.

4. A process for the preparation of an isothiazole derivative of the formula (I) according to claim 1 comprising
(a) for compounds of the formula (I) in which
A represents a group of the formula

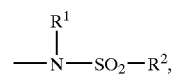

wherein $R^1$ and $R^2$ have the same meanings as for formula (I), reacting 3,4-dichloroisothiazole-5-carbonyl chloride of the formula (II)

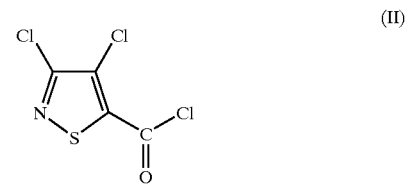

with a sulfonylamino compound of the formula (III)

in which $R^1$ and $R^2$ have the same meanings as for formula (I), in the presence of an inert diluent and optionally in the presence of an acid-binding agent; or (b) for compounds of the formula (I) in which
A represents a group of the formula

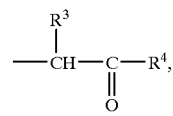

wherein $R^3$ and $R^4$ have the same meanings as for formula (I), reacting 3,4-dichloro-isothiazole-5-carbonyl chloride of the formula (II)

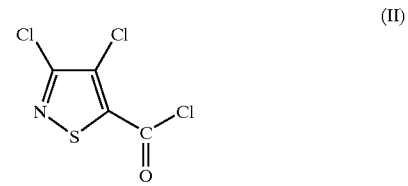

with a carbonyl compound of the formula (IV)

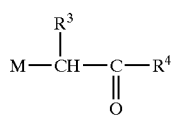

(IV)

in which
R³ and R⁴ have the same meanings as for formula (I), and
M represents lithium, sodium, or potassium, in the presence of an inert diluent and optionally in the presence of an acid-binding agent; or
(c) for compounds of the formula (I) in which
A represents a group of the formula

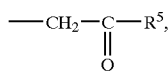

wherein R⁵ has the same meaning as for formula (I), reacting an isothiazolecarboxylic acid derivative of the formula (V)

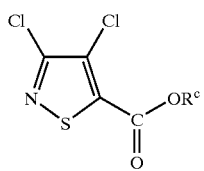

(V)

in which R$^c$ represents C$_{1-4}$ alkyl, with a ketone of the formula

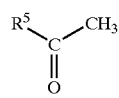

(VI)

in which R⁵ has the same meaning as for formula (I), in the presence of an inert diluent and optionally in the presence of an acid-binding agent; or (d) for compounds of the formula (I) in which
A represents a group of the formula

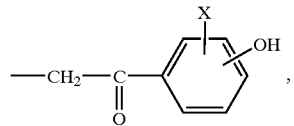

wherein X represents hydrogen or halogen, reacting an isothiazole derivative of the formula (I')

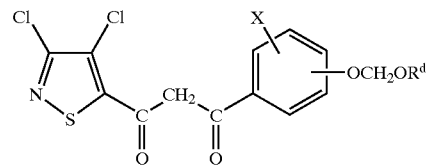

(I')

in which
X represents hydrogen or halogen, and
R$^d$ represents C$_{1-4}$ alkyl,
in the presence of water and an inert organic diluent and optionally in the presence of an acid catalyst.

5. A microbicidal composition comprising at least one isothiazole derivative of the formula (I) according to claim 1 and one or more extenders and/or surface active agents.

6. A process for combating undesired microorganisms comprising applying an isothiazole derivative of the formula (I) according to claim 1 to the microorganisms and/or to the habitat of the microorganisms.

7. A process for the preparation of a microbicidal composition comprising mixing an isothiazole derivative of the formula (I) according to claim 1 with one or more extenders and/or surface active agents.

* * * * *